US012687521B1

(12) United States Patent
Zhu et al.

(10) Patent No.: US 12,687,521 B1
(45) Date of Patent: Jul. 21, 2026

(54) REAL-TIME PHOTOACOUSTIC MICROSCOPY FOR RAPID DIAGNOSIS OF PATHOLOGY

(71) Applicant: Novateur Research Solutions, Ashburn, VA (US)

(72) Inventors: Xiaoyi Zhu, Alhambra, CA (US); Lingyi Zhao, Ashburn, VA (US); Khurram Hassan-Shafique, Aldie, VA (US); Zeeshan Rasheed, Great Falls, VA (US)

(73) Assignee: Novateur Research Solutions, Ashburn, VA (US)

( * ) Notice: Subject to any disclaimer, the term of this patent is extended or adjusted under 35 U.S.C. 154(b) by 0 days.

(21) Appl. No.: 19/387,620

(22) Filed: Nov. 12, 2025

(51) Int. Cl.
| | |
|---|---|
| *G01N 29/24* | (2006.01) |
| *G01N 29/06* | (2006.01) |
| *G01N 29/22* | (2006.01) |
| *G01N 33/483* | (2006.01) |
| *G06V 10/26* | (2022.01) |
| *G06V 10/82* | (2022.01) |
| *G06V 20/69* | (2022.01) |

(52) U.S. Cl.
CPC ..... *G01N 29/2418* (2013.01); *G01N 29/0654* (2013.01); *G01N 29/225* (2013.01); *G01N 33/4833* (2013.01); *G06V 10/26* (2022.01); *G06V 10/82* (2022.01); *G06V 20/693* (2022.01); *G06V 20/695* (2022.01); *G01N 2291/02475* (2013.01); *G06V 2201/03* (2022.01)

(58) Field of Classification Search
CPC ........... G01N 29/2418; G01N 29/0654; G01N 29/225; G01N 33/4833; G01N 2291/02475; G06V 20/695; G06V 10/82; G06V 2201/03; G06V 10/26; G06V 20/693

See application file for complete search history.

(56) References Cited

U.S. PATENT DOCUMENTS

| | | | | |
|---|---|---|---|---|
| 11,122,978 | B1 * | 9/2021 | Haji Reza | .......... G01N 21/1702 |
| 11,786,128 | B2 * | 10/2023 | Haji Reza | .......... G01N 21/6456 600/425 |
| 12,050,201 | B2 | 7/2024 | Wang et al. | |
| 12,299,875 | B2 * | 5/2025 | Wong | .................... G06T 7/0012 |
| 12,482,280 | B2 * | 11/2025 | Marie-Nelly | .......... G06V 20/69 |
| 12,504,363 | B2 * | 12/2025 | Wang | ................. G01N 21/1702 |

(Continued)

*Primary Examiner* — Octavia Hollington
(74) *Attorney, Agent, or Firm* — Rahman LLC

(57) ABSTRACT

A photoacoustic microscopy system and method for rapid intraoperative pathology imaging comprises a pulsed ultraviolet laser source, a polygon scanner for high-speed beam deflection, a telephoto lens assembly, an objective lens and a motorized stage with multi-axis motion capability. A controller performs a rapid pre-scan to extract surface topology data and generate a contour map, then executes a high-resolution imaging scan while dynamically adjusting the tissue sample position based on the contour map to maintain focus across uneven surfaces. An ultrasound transducer detects photoacoustic signals in transmission or reflection modes. A conditional diffusion model is used to generate virtual histologically-stained images and a semantic segmentation network for automated tumor margin detection, enabling real-time pathological assessment during surgical procedures without chemical staining or tissue processing.

22 Claims, 18 Drawing Sheets

(56)    References Cited

U.S. PATENT DOCUMENTS

| | | | |
|---|---|---|---|
| 2023/0055979 A1 | 2/2023 | Wang et al. | |
| 2024/0020955 A1* | 1/2024 | Frick | G06T 11/10 |
| 2024/0255427 A1* | 8/2024 | Haji Reza | G01N 21/6486 |
| 2024/0371184 A1* | 11/2024 | Comiter | G06N 3/0475 |
| 2025/0164387 A1 | 5/2025 | Yao | |

* cited by examiner

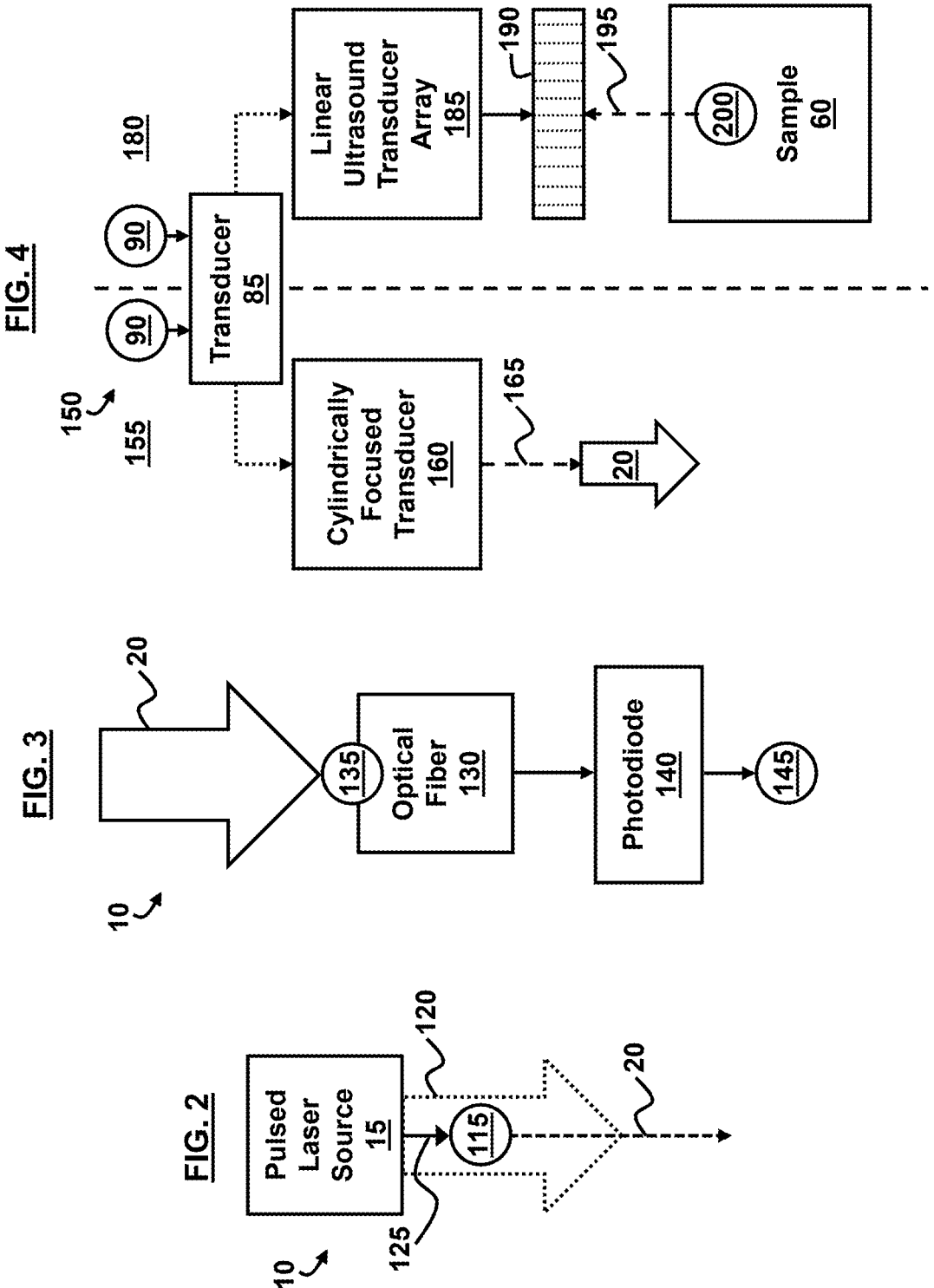

Transmission Mode

150

Reflection Mode - Slit-Aperture Cylindrical Transducer
205a

Reflection Mode - Prism-based ultrasound transducer
205b

A

310

312
Raster scanning the ultraviolet laser beam across the tissue sample with a reduced resolution relative to a subsequent high-resolution imaging scan 314
Detecting photoacoustic signals generated during the pre-scan 316
Extracting surface topology information from time-of-flight data contained in the photoacoustic signals to generate a contour map

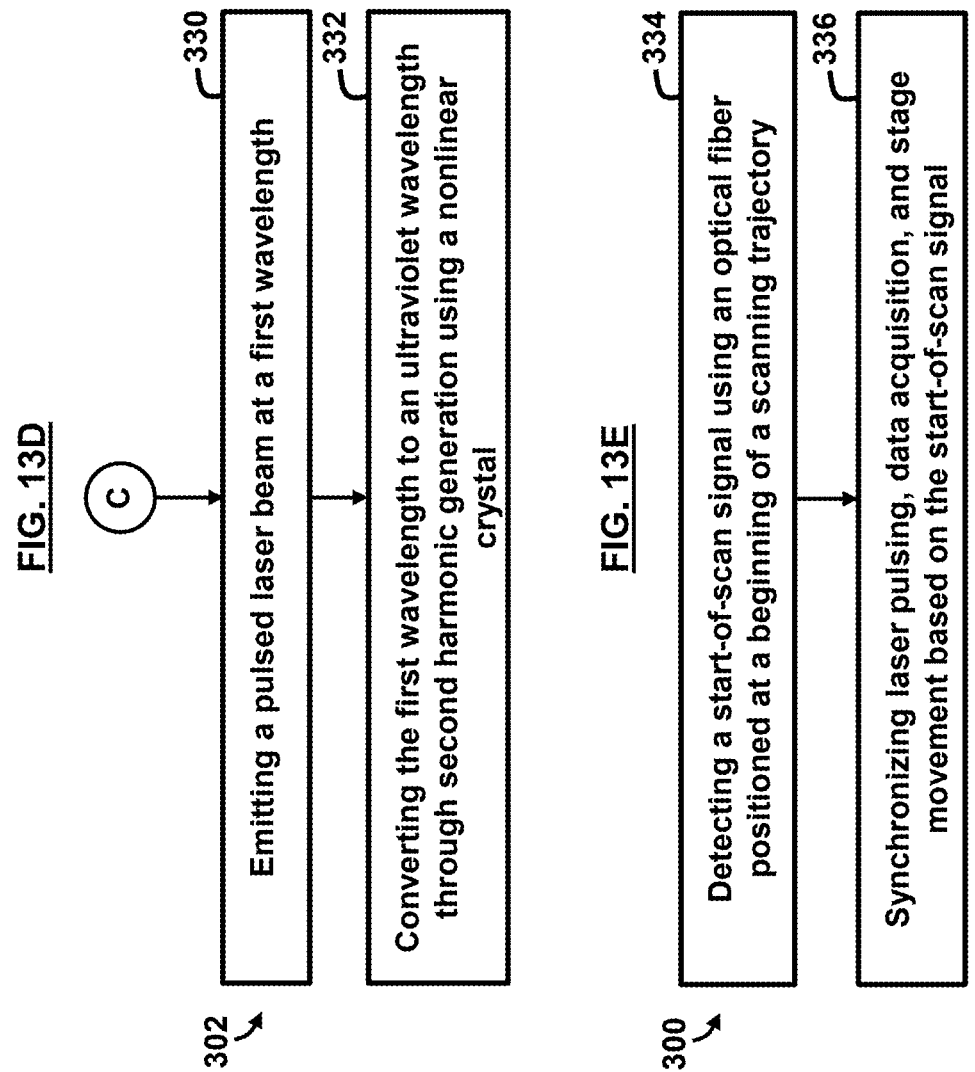

FIG. 13D

330 — Emitting a pulsed laser beam at a first wavelength

332 — Converting the first wavelength to an ultraviolet wavelength through second harmonic generation using a nonlinear crystal

334 — Detecting a start-of-scan signal using an optical fiber positioned at a beginning of a scanning trajectory 336 — Synchronizing laser pulsing, data acquisition, and stage movement based on the start-of-scan signal

300

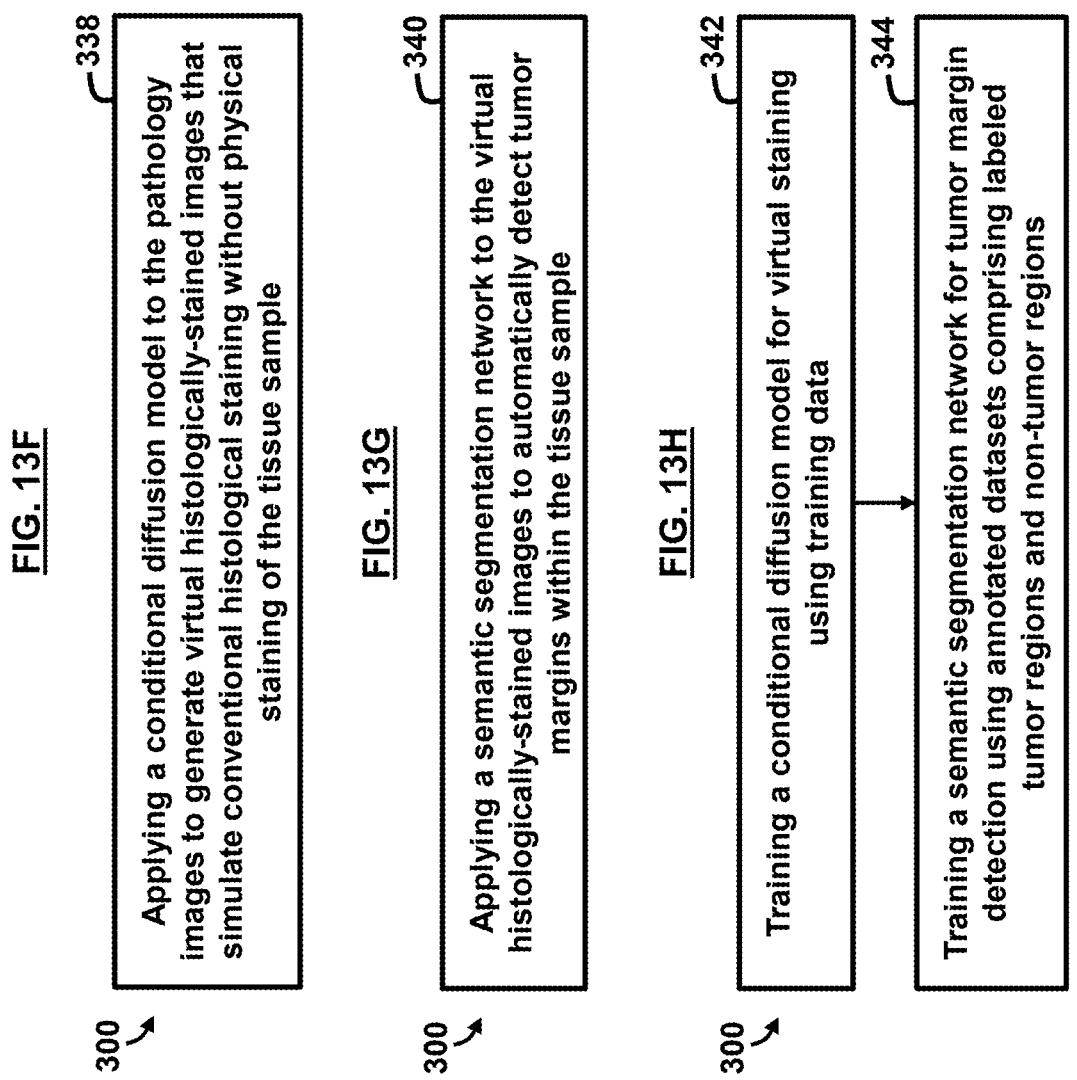

338 — Applying a conditional diffusion model to the pathology images to generate virtual histologically-stained images that simulate conventional histological staining without physical staining of the tissue sample

340 — Applying a semantic segmentation network to the virtual histologically-stained images to automatically detect tumor margins within the tissue sample

342 — Training a conditional diffusion model for virtual staining using training data 344 — Training a semantic segmentation network for tumor margin detection using annotated datasets comprising labeled tumor regions and non-tumor regions

FIG. 14B

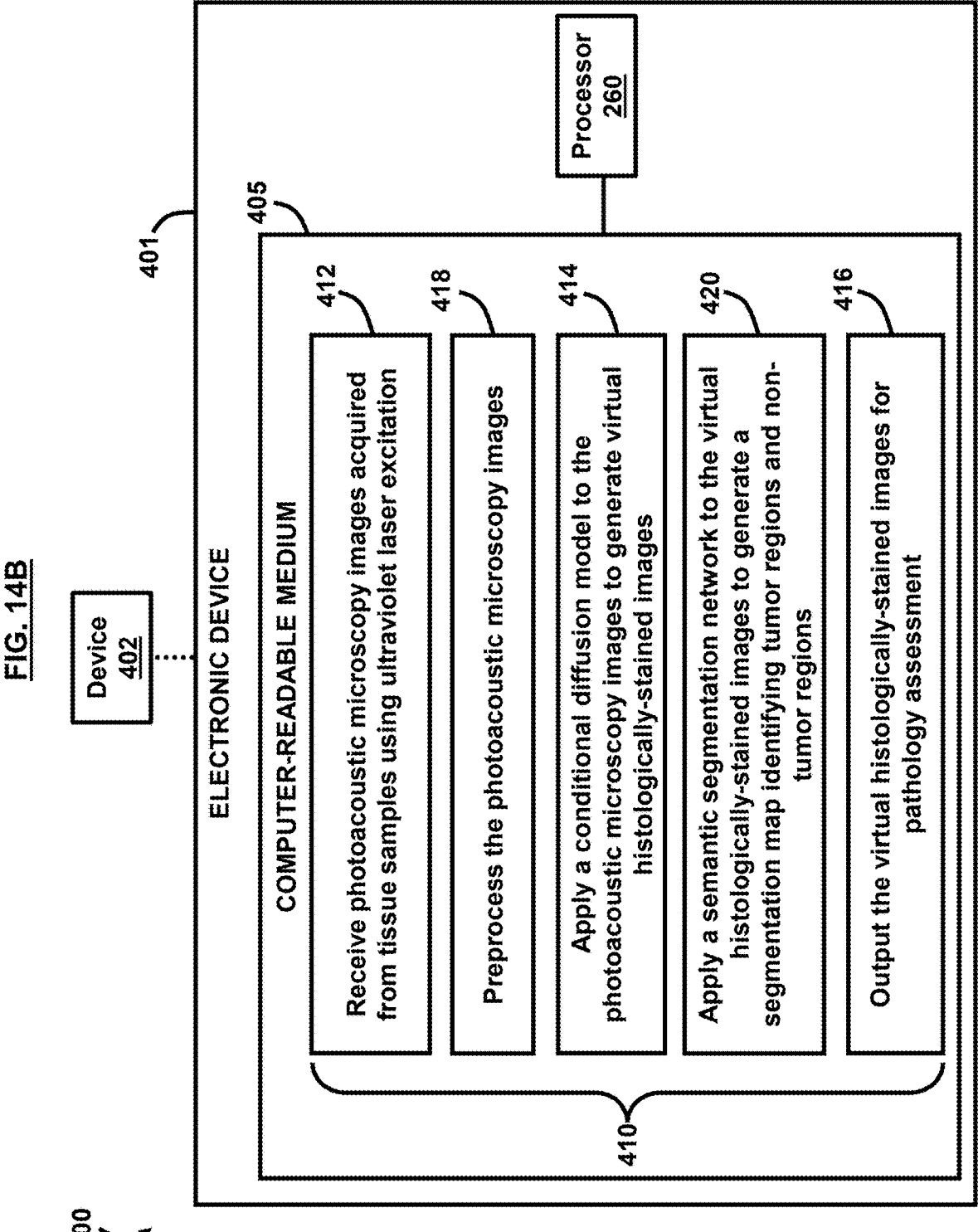

400

401 — ELECTRONIC DEVICE

Device 402

Processor 260

405 — COMPUTER-READABLE MEDIUM

410

412 — Receive photoacoustic microscopy images acquired from tissue samples using ultraviolet laser excitation 418 — Preprocess the photoacoustic microscopy images 414 — Apply a conditional diffusion model to the photoacoustic microscopy images to generate virtual histologically-stained images 420 — Apply a semantic segmentation network to the virtual histologically-stained images to generate a segmentation map identifying tumor regions and non-tumor regions 416 — Output the virtual histologically-stained images for pathology assessment

FIG. 16

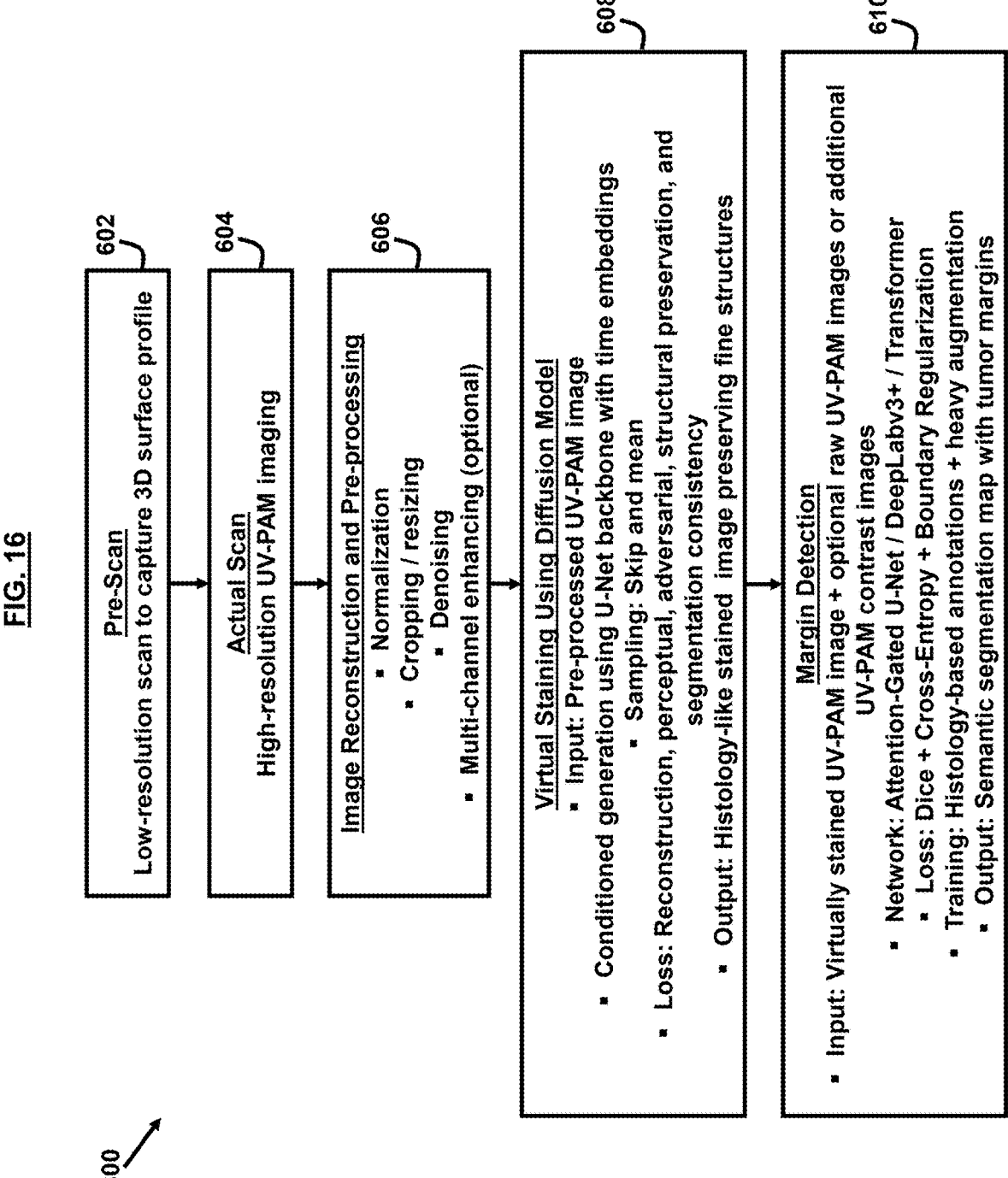

Pre-Scan
Low-resolution scan to capture 3D surface profile — 602

Actual Scan
High-resolution UV-PAM imaging — 604

Image Reconstruction and Pre-processing — 606
- Normalization
- Cropping / resizing
- Denoising
- Multi-channel enhancing (optional)

Virtual Staining Using Diffusion Model — 608
- Input: Pre-processed UV-PAM image
  - Conditioned generation using U-Net backbone with time embeddings
  - Sampling: Skip and mean
- Loss: Reconstruction, perceptual, adversarial, structural preservation, and segmentation consistency
- Output: Histology-like stained image preserving fine structures

Margin Detection — 610
- Input: Virtually stained UV-PAM image + optional raw UV-PAM images or additional UV-PAM contrast images
  - Network: Attention-Gated U-Net / DeepLabv3+ / Transformer
  - Loss: Dice + Cross-Entropy + Boundary Regularization
  - Training: Histology-based annotations + heavy augmentation
- Output: Semantic segmentation map with tumor margins

600

REAL-TIME PHOTOACOUSTIC MICROSCOPY FOR RAPID DIAGNOSIS OF PATHOLOGY

BACKGROUND

Technical Field

The embodiments herein generally relate to medical imaging systems and methods for intraoperative pathology assessment, and more particularly to photoacoustic microscopy systems and methods.

Description of the Related Art

This background description includes information that may be useful in understanding the present invention. It is not an admission that any of the information provided herein is prior art or relevant to the presently claimed invention or that any publication specifically or implicitly referenced is prior art.

In the field of surgical oncology, rapid and accurate histopathological evaluation is essential for guiding intraoperative decision-making and optimizing patient outcomes. For example, in breast-conserving surgery, precise assessment of tumor margins is critical to ensure complete tumor removal while avoiding excessive tissue excision that could necessitate repeat procedures. The ability to obtain real-time pathology information during surgery can significantly impact surgical outcomes, reduce the need for subsequent operations, and improve patient prognosis.

Currently, intraoperative pathology predominantly relies on frozen section analysis. While widely adopted as the standard of care, frozen section analysis presents several significant limitations that compromise its effectiveness. First, the technique often introduces artifacts into the tissue that can obscure cellular details and complicate pathological interpretation. Second, the process results in tissue loss during sectioning, which may affect subsequent pathological analysis and diagnosis. Third, frozen section analysis is generally unsuitable for certain tissue types, particularly fatty or calcified tissues, where the freezing and sectioning process produces poor-quality specimens. Fourth, and perhaps most critically, the process typically requires more than 20 minutes to complete, thereby extending surgical duration and increasing the associated risks to patients, including infection, anesthesia complications, and increased healthcare costs. Despite these substantial drawbacks, frozen section analysis remains the standard method for intraoperative pathology due to the lack of viable alternatives that can match both its speed and diagnostic utility.

On the other hand, hematoxylin and eosin (H&E) staining represents the current gold standard for definitive histopathological analysis in pathology. However, H&E staining requires complex, multi-step tissue processing procedures including fixation, dehydration, embedding, sectioning, and staining. This comprehensive workflow typically takes 24 hours or more to produce final results, making it entirely impractical for intraoperative use where surgical decisions must be made within minutes.

Recent advances in high-resolution optical imaging techniques have introduced promising alternatives to conventional intraoperative pathology. Notable among these emerging technologies are microscopy with ultraviolet surface excitation (MUSE), light sheet microscopy, and stimulated Raman scattering (SRS) microscopy. However, each of these techniques presents specific limitations that hinder their widespread adoption in intraoperative pathology settings. For example, MUSE generally requires exogenous staining with fluorescent dyes to generate sufficient histological contrast, which complicates the workflow, adds processing time, and introduces additional steps that reduce the speed advantage over frozen sections. Light sheet microscopy, while capable of producing high-quality three-dimensional images, is fundamentally limited by its reliance on optical tissue transparency. Achieving the necessary transparency requires complex and time-consuming tissue clearing procedures that can take hours or even days, rendering this approach unsuitable for time-sensitive intraoperative applications. SRS microscopy offers label-free imaging with high molecular specificity by exploiting intrinsic molecular vibrations, but its relatively slow imaging speed and is generally limited by the point-scanning nature of the technique and the need for high signal-to-noise ratios. This significantly constrains its utility in time-sensitive surgical environments where rapid tissue assessment is paramount.

Photoacoustic microscopy (PAM) has emerged as a potentially viable alternative imaging modality for intraoperative pathology by enabling label-free imaging through the detection of optical absorption-induced acoustic signals. In this technique, pulsed laser light is absorbed by tissue chromophores, causing rapid localized heating and thermoelastic expansion that generates ultrasonic waves. These ultrasound waves (also called photoacoustic signals) are detected by ultrasound transducers and reconstructed into images that reveal the spatial distribution of optical absorbers within the tissue. In particular, ultraviolet photoacoustic microscopy (UV-PAM) leverages the strong natural absorption of nucleic acids (e.g., DNA and RNA) and proteins in the ultraviolet spectral range (particularly around 266 nm wavelength) to achieve high-contrast, high-resolution pathology imaging without requiring any chemical staining or tissue processing. UV-PAM has demonstrated significant potential in generating imaging results equivalent to H&E staining for various tissue types including bone and breast tissue specimens.

Unlike frozen section analysis, UV-PAM does not require freezing, physical sectioning, or other destructive tissue processing steps. Instead, it enables direct imaging of fresh tissue surfaces at subcellular resolution, providing rapid, artifact-free assessment while fully preserving sample integrity for subsequent testing and analysis. This preservation of tissue is particularly valuable for molecular diagnostics, genomic analysis, and other downstream testing that may be required. Additionally, in challenging clinical cases such as bone and soft tissue sarcomas, where frozen sectioning is impractical or impossible due to tissue hardness, UV-PAM remains fully applicable because it does not require any physical sectioning of the specimen.

However, despite these advantages, the widespread clinical adoption of UV-PAM technology has been severely limited by fundamental technical challenges that prevent it from achieving the imaging speeds necessary for practical intraoperative use. These limitations stem from several interconnected factors. First, conventional ultraviolet pulsed lasers suitable for photoacoustic excitation operate at relatively low pulse repetition rates, typically in the kilohertz range or lower. Since each laser pulse generates one data point in the image, low repetition rates directly translate to slow image acquisition speeds that are incompatible with the time constraints of surgical procedures. Second, most conventional UV-PAM systems rely on relatively slow mechanical raster-scanning (e.g., motorized translation stages) for point-by-point acquisition. Although faster scanners (e.g., MEMS mirrors, galvanometers) have been adopted in PAM to improve speed, they typically involve trade-offs such as reduced FOV and reduced sampling density, which still limits their use in large-area, high-throughput intraoperative applications. Third, the uneven and irregular surface topography characteristic of fresh, unprocessed surgical tissue specimens poses significant challenges for maintaining consistent high-resolution imaging over wide areas. In optical microscopy, high resolution requires tight focusing, which creates a shallow depth of focus. When height variations of imaging surfaces exceed this depth of focus, regions of the specimen will be out of focus, resulting in degraded image quality that compromises diagnostic accuracy.

Various prior art approaches have attempted to address these limitations with limited success. One approach, described in U.S. Pat. No. 12,050,201, employs multi-focus photoacoustic microscopy that achieves higher imaging speed by splitting a single laser beam into multiple foci and using an ultrasound transducer array for parallel detection of signals from multiple points simultaneously. However, this approach is generally costly because it requires expensive transducer arrays and multi-channel data acquisition systems with many parallel signal processing channels. Moreover, it generally relies on computationally intensive image reconstruction algorithms that can require hours of processing time to generate final images from the raw data. While the physical scanning step may be fast, this heavy post-processing requirement fundamentally undermines real-time usability in the operating room where immediate results are essential. Furthermore, because multiple foci must all lie in the same imaging plane to enable parallel high-resolution imaging, this method may not be suited for samples with uneven surfaces, which are precisely the type of specimens encountered in surgical pathology.

Another approach, described in U.S. Patent Application Publication No. 2023/0055979, proposes to improve imaging quality for uneven tissue surfaces by extracting surface topology information from photoacoustic signals and dynamically adjusting the vertical position of the sample or optical system to maintain focus during imaging. While this addresses the surface topography problem, it relies on raster scanning in all three dimensions using motorized stages, which inherently limits the overall imaging speed. Moreover, because the surface height must be dynamically adjusted during the actual imaging process itself, the speed constraints of mechanical stage movement further reduce the maximum achievable imaging rate.

Yet another approach, described in U.S. Patent Application Publication No. 2025/0164387, employs a polygon scanner containing a rotating multi-faceted mirror for high-speed laser beam scanning along one axis. While polygon scanners can indeed enable faster scanning compared to traditional galvanometer mirrors or mechanical translation stages, in this system the laser beam scanned by the polygon mirror is directed straight into the objective lens without intermediate beam conditioning optics. This configuration generally results in excessive angular spread of the scanned beam and produces a limited effective beam size constrained by the polygon mirror's aperture dimensions. These optical deficiencies can degrade the achievable spatial resolution and introduce geometric distortions across the field of view, preventing the system from maintaining the high resolution necessary for diagnostic-quality pathology imaging across wide tissue areas.

SUMMARY

In view of the foregoing, an embodiment herein provides a photoacoustic microscopy system for intraoperative pathology imaging, the system comprising a pulsed laser source that generates an ultraviolet laser beam; a polygon scanner having a plurality of reflective facets, wherein the polygon scanner deflects the ultraviolet laser beam along a fast axis; a telephoto lens assembly that receives the deflected ultraviolet laser beam from the polygon scanner, wherein the telephoto lens assembly comprising a positive lens group and a negative lens group that expand the deflected ultraviolet laser beam; an objective lens configured to focus the expanded ultraviolet laser beam onto a tissue sample; a motorized stage having at least two axes of motion, including at least one axis of an imaging plane and an axis orthogonal to the imaging plane, wherein the motorized stage is configured to support the tissue sample and configured to translate the tissue sample along the at least one axis of the imaging plane and vertically along the orthogonal axis; an ultrasound transducer that is configured to detect photoacoustic signals generated from the tissue sample in response to illumination by the ultraviolet laser beam; a data acquisition device that digitizes the photoacoustic signals; and a controller that controls the motorized stage and is configured to perform a rapid pre-scan of the tissue sample; extracts surface topology data from the photoacoustic signals acquired during the pre-scan to generate a contour map representing variations in surface height of the tissue sample; synchronizes operation of the pulsed laser source, the polygon scanner, the motorized stage, and the data acquisition device during imaging; and controls the motorized stage and is configured to dynamically adjust a position of the tissue sample vertically along the orthogonal axis during a high-resolution imaging scan based on the contour map.

The system may further comprise a nonlinear crystal positioned in an optical path of a laser beam at a first wavelength emitted by the pulsed laser source, wherein the nonlinear crystal converts the laser beam of the first wavelength to generate the ultraviolet laser beam through harmonic generation. The system may further comprise an optical fiber having a stripped tip positioned at a beginning of a scanning trajectory of the ultraviolet laser beam; and a photodiode optically coupled to the optical fiber, wherein the photodiode generates a start-of-scan timing signal when the deflected ultraviolet laser beam strikes the stripped tip of the optical fiber.

The ultrasound transducer may detect the photoacoustic signals in a transmission mode of signal detection; in a first configuration, the ultrasound transducer comprises a cylindrically focused transducer providing a one-dimensional (1D) line focus for signal detection, wherein the ultraviolet laser beam is confocal with the 1D line focus and is scanned along the 1D line focus; and in a second configuration, the ultrasound transducer is arranged in a linear ultrasound transducer array such that each transducer element detects signals from a corresponding illuminated spot on the tissue sample, thereby allowing direct spatial mapping of signals without requiring heavy image reconstruction algorithms.

The ultrasound transducer may detect photoacoustic signals in a reflection mode of signal detection, and the ultrasound transducer may comprise a cylindrically focused transducer element having a central rectangular slit aperture that permits coaxial transmission of the ultraviolet laser beam therethrough. In another approach, the reflection-mode signal detection assembly may comprise a right-angle prism and a rhomboid prism separated by an optical coupling medium, wherein the ultrasound transducer is to detect photoacoustic signals in a reflection mode of signal detection, wherein the rhomboid prism includes an acoustic cylindrical lens ground into a surface thereof, wherein the right-angle prism includes an optical correction lens ground on a top surface thereof, wherein the ultrasound transducer is mounted on the rhomboid prism and acoustically coupled thereto, and wherein the right-angle prism and the rhomboid prism guide the ultraviolet laser beam and acoustic waves to a common focal region.

The system may further comprise a processor that executes a conditional diffusion model comprising a neural network, wherein the processor transforms photoacoustic microscopy images into virtual histologically-stained images. The processor may execute a semantic segmentation network to identify tumor regions and non-tumor regions in the virtual histologically-stained images.

Another embodiment provides a method for rapid intraoperative pathology imaging, the method comprising generating an ultraviolet laser beam; deflecting the ultraviolet laser beam using a rotating polygon scanner along a fast axis; directing the deflected ultraviolet laser beam through a telephoto lens assembly comprising a positive lens group and a negative lens group to expand the deflected ultraviolet laser beam; focusing the expanded ultraviolet laser beam onto a surface of a tissue sample using an objective lens; performing a pre-scan of the tissue sample by raster scanning the ultraviolet laser beam across the tissue sample with a reduced resolution relative to a subsequent high-resolution imaging scan, detecting photoacoustic signals generated during the pre-scan, and extracting surface topology information from time-of-flight data contained in the photoacoustic signals to generate a contour map. The method may further comprise performing a high-resolution imaging scan by raster scanning the ultraviolet laser beam across the tissue sample, dynamically adjusting a position of the tissue sample along an orthogonal axis in real-time based on the contour map to maintain the surface within an optical depth of focus, and detecting photoacoustic signals to generate pathology images.

Generating the ultraviolet laser beam may comprise emitting a pulsed laser beam at a first wavelength; and converting the first wavelength to an ultraviolet wavelength through second harmonic generation using a nonlinear crystal. The method may further comprise detecting a start-of-scan signal using an optical fiber positioned at the beginning of a scanning trajectory; and synchronizing laser pulsing, data acquisition, and stage movement based on the start-of-scan signal. Detecting photoacoustic signals may comprise detecting the photoacoustic signals in transmission mode using a cylindrically focused ultrasound transducer positioned opposite to an illumination side of the tissue sample. Detecting photoacoustic signals may comprise detecting the photoacoustic signals in reflection mode through a cylindrically focused ultrasound transducer with a slit aperture, wherein the ultraviolet laser beam passes coaxially through the slit aperture.

The method may further comprise applying a conditional diffusion model to the pathology images to generate virtual histologically-stained images that simulate conventional histological staining without physical staining of the tissue sample. The method may further comprise applying a semantic segmentation network to the virtual histologically-stained images to automatically detect tumor margins within the tissue sample. The method may further comprise training a conditional diffusion model for virtual staining using training data comprising photoacoustic microscopy images acquired with ultraviolet laser excitation; and corresponding histologically-stained images, wherein the conditional diffusion model is trained using a loss function comprising at least one of reconstruction loss, perceptual loss, adversarial loss, structural preservation loss, or segmentation consistency loss. The method may further comprise training a semantic segmentation network for tumor margin detection using annotated datasets comprising labeled tumor regions and non-tumor regions.

Another embodiment provides a non-transitory computer-readable medium storing instructions that, when executed by a processor, cause the processor to receive photoacoustic microscopy images acquired from tissue samples using ultraviolet laser excitation; apply a conditional diffusion model to the photoacoustic microscopy images to generate virtual histologically-stained images, wherein the conditional diffusion model comprises a denoising neural network trained to reverse a forward diffusion process while being conditioned on the photoacoustic microscopy images; and output the virtual histologically-stained images for pathology assessment.

The instructions may cause the processor to preprocess the photoacoustic microscopy images prior to applying the conditional diffusion model by performing at least one of background flattening, global intensity normalization, filter-based denoising, or multi-channel enhancement. The conditional diffusion model may generate virtual histologically-stained images at a higher resolution than the photoacoustic microscopy images through learned upsampling. The instructions may cause the processor to apply a semantic segmentation network to the virtual histologically-stained images to generate a segmentation map identifying tumor regions and non-tumor regions. The semantic segmentation network may receive as input both the virtual histologically-stained images and the photoacoustic microscopy images. The semantic segmentation network may be trained using a loss function comprising at least one of Dice loss, cross-entropy loss, or boundary-aware regularization terms.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2 is a block diagram illustrating wavelength conversion components of the photoacoustic microscopy system including a nonlinear crystal for harmonic generation, according to an embodiment herein;

FIG. 3 is a block diagram illustrating a start-of-scan detection system comprising an optical fiber and photodiode for synchronization, according to an embodiment herein;

FIG. 4 is a block diagram illustrating transmission mode detection configurations for the ultrasound transducer including a cylindrically focused transducer and a linear transducer array, according to an embodiment herein;

FIG. 8 is a schematic block diagram illustrating the overall system architecture showing the laser excitation module, high-speed scanning module, and ultrasound detection module with detailed optical path components, according to an embodiment herein;

FIG. 13D is a flow diagram illustrating wavelength conversion steps for generating the ultraviolet laser beam through second harmonic generation, according to an embodiment herein;

FIG. 13E is a flow diagram illustrating start-of-scan signal detection and synchronization steps, according to an embodiment herein;

FIG. 13F is a flow diagram illustrating the application of a conditional diffusion model for virtual staining, according to an embodiment herein;

FIG. 13G is a flow diagram illustrating the application of a semantic segmentation network for tumor margin detection, according to an embodiment herein;

FIG. 13H is a flow diagram illustrating training processes for the conditional diffusion model and semantic segmentation network, according to an embodiment herein;

FIG. 14B is a block diagram illustrating a non-transitory computer-readable medium and processor architecture for executing virtual staining with preprocessing and segmentation operations, according to an embodiment herein;

FIG. 16 is a data pipeline diagram illustrating the complete workflow from pre-scan through high-resolution imaging, image preprocessing, virtual staining using a diffusion model, and margin detection, according to an embodiment herein.

Figure 1:
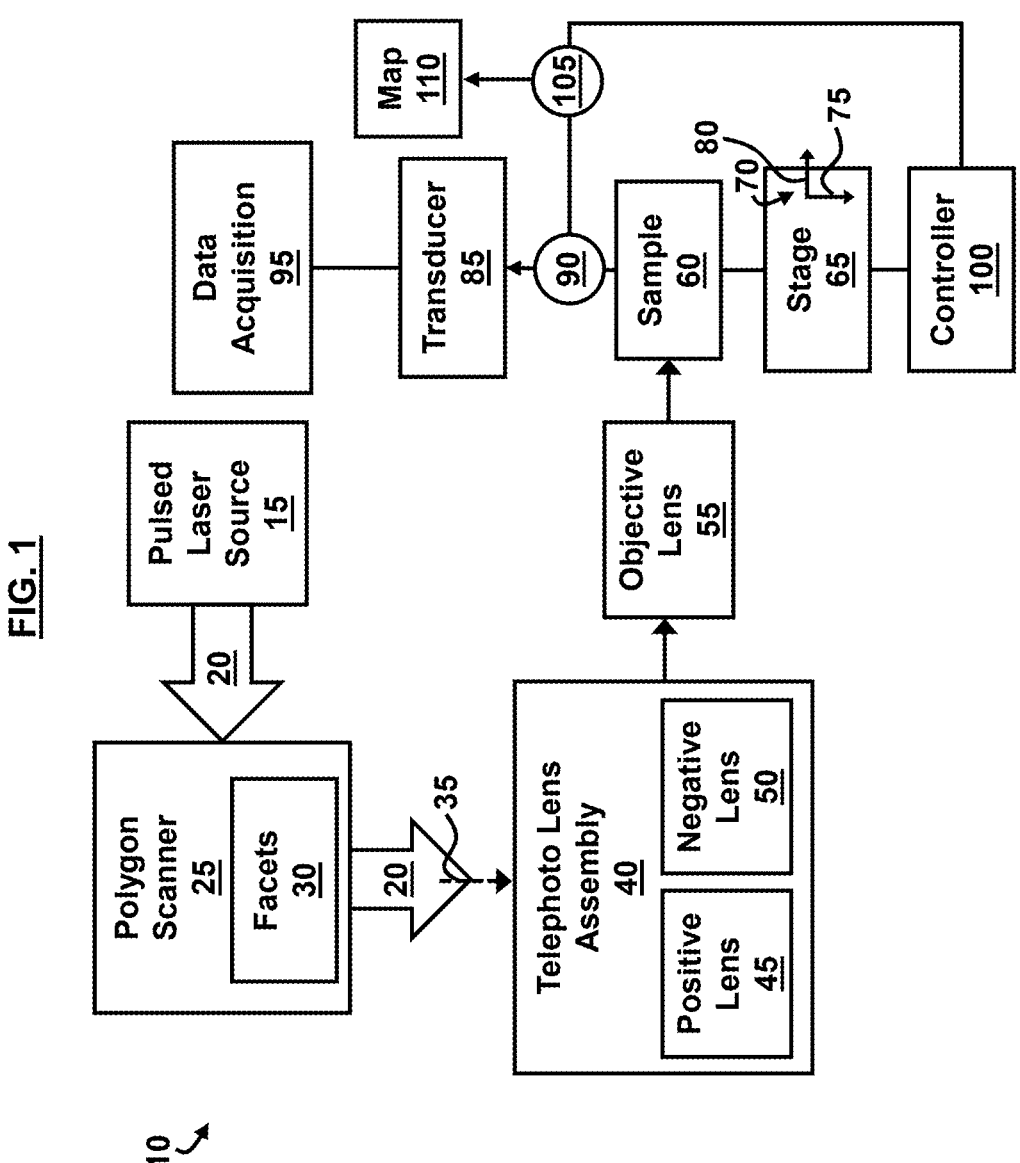
FIG. 1 is a block diagram illustrating a photoacoustic microscopy system for intraoperative pathology imaging, according to an embodiment herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. The following description of particular embodiment(s) is merely exemplary in nature and is in no way intended to limit the scope of the invention, its application, or uses, which can, of course, vary.

It will be understood that when an element or layer is referred to as being "on", "connected to", or "coupled to" another element or layer, it may be directly on, directly connected to, or directly coupled to the other element or layer, or intervening elements or layers may be present. In contrast, when an element or layer is referred to as being "directly on", "directly connected to", or "directly coupled to" another element or layer, there are no intervening elements or layers present. It will be understood that for the purposes of this disclosure, "at least one of X, Y, and Z" or "any of X, Y, and Z" may be construed as X only, Y only, Z only, or any combination of two or more items X, Y, and Z (e.g., XYZ, XY, XZ, YZ).

The description herein describes inventive examples to enable those skilled in the art to practice the embodiments herein and illustrates the best mode of practicing the embodiments herein. Upon reading the following description in light of the accompanying drawing figures, those skilled in the art will understand the concepts of the disclosure and will recognize applications of these concepts not particularly addressed herein.

The terms first, second, etc. may be used herein to describe various elements, but these elements should not be limited by these terms as such terms are only used to distinguish one element from another. For example, a first element could be termed a second element, and, similarly, a second element could be termed a first element, etc. without departing from the scope of the present disclosure. As used herein, the term "and/or" includes any and all combinations of one or more of the associated listed items.

Furthermore, although the terms "final", "first", "second", "upper", "lower", "bottom", "side", "intermediate", "middle", and "top", etc. may be used herein to describe various elements, but these elements should not be limited by these terms. These terms are only used to distinguish one element from another. For example, a first element could be termed a "top" element and, similarly, a second element could be termed a "top" element depending on the relative orientations of these elements.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. "Or" means "and/or." As used herein, the term "and/or" includes any and all combinations of one or more of the associated listed items. It will be further understood that the terms "comprises" and/or "comprising," or "includes" and/or "including" when used herein, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The embodiments described herein provide an ultraviolet laser excitation technique for rapid, label-free, high-resolution imaging of fresh tissue specimens during surgical procedures. Referring now to the drawings, and more particularly to FIGS. 1 through 16, where similar reference characters denote corresponding features consistently throughout the figures, there are shown preferred embodiments. In the drawings, the size and relative sizes of components, layers, and regions, etc. may be exaggerated for clarity.

FIG. 1 illustrates a photoacoustic microscopy system 10 for intraoperative pathology imaging that integrates multiple subsystems to enable rapid, high-resolution, label-free imaging of fresh tissue specimens during surgical procedures. The system 10 achieves clinically relevant imaging speeds through a combination of high-repetition-rate laser excitation, polygon-based beam scanning, and intelligent contour-compensated focusing that overcomes the fundamental speed limitations of conventional photoacoustic microscopy systems. The system 10 comprises a pulsed laser source 15 that generates an ultraviolet laser beam 20 at a wavelength specifically selected to coincide with the absorption maxima of nucleic acids and proteins in biological tissue. The term "ultraviolet" as used herein refers to electromagnetic radiation having wavelengths shorter than visible light, for example, in the range of 200 to 400 nanometers, with the preferred wavelength being 266 nanometers in accordance with the embodiments herein. At this wavelength, deoxyribonucleic acid (DNA) and ribonucleic acid (RNA) exhibit strong optical absorption due to electronic transitions in the aromatic nucleotide bases, while proteins absorb through their constituent aromatic amino acids including tryptophan, tyrosine, and phenylalanine. This wavelength selection enables visualization of cellular nuclei and cytoplasmic structures without any chemical staining, creating contrast mechanisms similar to conventional hematoxylin and eosin histology such that hematoxylin stains nuclei blue-purple.

The pulsed laser source 15 operates at pulse repetition frequencies substantially exceeding one megahertz, typically in the range of two to ten megahertz, which represents a dramatic improvement over conventional ultraviolet lasers used in photoacoustic microscopy that typically operate at kilohertz repetition rates. This high repetition rate helps achieve the rapid imaging speeds required for intraoperative applications where surgical decisions must be made within minutes.

The system 10 further comprises a polygon scanner 25 having a plurality of reflective facets 30 arranged in a regular polygonal configuration around a central axis of rotation. The polygon scanner 25 functions as a high-speed beam deflector that rapidly sweeps the ultraviolet laser beam 20 along a fast axis 35, also referred to as the X-axis or laser-scanning axis of the imaging system 10. In an example, the polygon scanner 25 may comprise sixteen reflective facets 30, although other facet numbers ranging from eight to thirty-two facets may be employed depending on the specific application requirements and desired scan characteristics. Each reflective facet 30 comprises a flat mirror surface with high reflectivity at ultraviolet wavelengths, achieved through either metallic coatings such as aluminum or enhanced aluminum, or through dielectric multilayer coatings specifically designed for 266 nm wavelength. As the polygon scanner 25 rotates continuously at constant angular velocity, each facet 30 sequentially intercepts the incident ultraviolet laser beam 20 and deflects it through a predetermined angular range. The angular deflection varies continuously during the active period of each facet 30, causing the reflected beam to sweep across the imaging field along the fast axis 35. With sixteen facets 30 rotating at 45,000 revolutions per minute, the system 10 can achieve 12,000 line scans per second, which is orders of magnitude faster than galvanometer-based scanning systems or mechanical translation stages employed in conventional photoacoustic microscopy systems.

The polygon scanner 25 provides unique features over alternative beam scanning technologies that make it uniquely suited for high-speed intraoperative photoacoustic pathology imaging. Unlike galvanometer scanners that employ oscillating mirrors which must continuously accelerate, decelerate, and reverse direction during each scan cycle, the polygon scanner 25 rotates with constant angular velocity without any velocity variations across the scan range. This constant velocity ensures uniform spatial sampling and eliminates the velocity-dependent distortions that galvanometer systems suffer from operating in non-resonant modes. Furthermore, the scan range of the polygon scanner 25 remains constant regardless of rotational speed or environmental factors, whereas resonant galvanometer scanners can exhibit scan amplitude variations due to mechanical vibrations or temperature changes.

The deflected ultraviolet laser beam 20 from the polygon scanner 25 is received by a telephoto lens assembly 40 that performs beam conditioning operations to maintain high optical resolution across the entire scanning field. The telephoto lens assembly 40 comprises a positive lens group 45 and a negative lens group 50 arranged in a telephoto configuration that provides beam expansion while compressing the angular spread of the scanned beam. The arrangement of the positive lens group 45 and negative lens group 50 may be implemented as a Galilean beam expander such that the negative lens group 50 precedes the positive lens group 45, or alternatively as a traditional telephoto arrangement such that the positive lens group 45 precedes the negative lens group 50, depending on the specific optical design optimization. The term "telephoto" as used herein refers to a compound lens system employing both positive and negative optical power to achieve beam expansion with reduced physical length compared to simple relay systems using only positive elements. In a Galilean-type configuration, the diverging negative lens group 50 first expands the collimated beam from the polygon scanner 25, and the converging positive lens group 45 then re-collimates the diverging beam at a larger diameter, with the feature that no intermediate focus is formed between the lenses 45, 50, reducing potential for air breakdown or dust contamination at high intensities.

The beam expansion performed by the telephoto lens assembly 40 serves multiple functions in maintaining high imaging resolution across wide fields of view. The specific lens power combination and spacing of the telephoto configuration, whether implemented with negative-positive ordering (Galilean) or positive-negative ordering (traditional telephoto), achieves the dual functions of diameter expansion and angular compression required for optimal scanning performance. First, the telephoto lens assembly 40 expands the beam diameter to completely fill the entrance pupil of the objective lens 55, thereby maximizing the effective numerical aperture of the focusing system 10. The numerical aperture, defined as the sine of the half-angle of the light cone that can be accepted by the lens multiplied by the refractive index of the medium, directly determines the achievable spatial resolution through the Abbe diffraction limit. By filling the objective lens aperture, the telephoto lens assembly 40 ensures that the system achieves its maximum theoretical resolution capability. Second, the telephoto lens assembly 40 reduces the angular spread of the scanned beam 20 as it propagates toward the objective lens 55, which maintains telecentric imaging conditions at the sample plane. Telecentricity means that the main rays of the focused spots are perpendicular to the image plane regardless of their position in the field of view, ensuring that the spot size and shape remain constant across the entire scan range without geometric distortions or magnification variations. Third, the telephoto lens assembly 40 mitigates field curvature aberrations that would otherwise cause the focal plane to curve away from the flat sample surface, resulting in defocused regions at the edges of the field of view.

The telephoto configuration of the lens assembly 40 contains unique features compared with alternative beam expansion approaches such as simple relay lens systems composed of two positive lenses. A relay system using two positive lenses would require a physical length approximately equal to the sum of their focal lengths to achieve the same beam expansion ratio, resulting in a long and bulky optical assembly. In contrast, the telephoto lens assembly 40 achieves equivalent beam expansion with a much shorter physical length due to the negative power of the second lens group 50, which effectively "folds" the optical path. This compact configuration is particularly valuable for intraoperative pathology applications where the imaging system 10 must be integrated into a crowded surgical environment with limited space around the operative field. The reduced system length also decreases the overall weight and moment of inertia of the scanning system 10, improving mechanical stability and reducing vibration sensitivity. Furthermore, the configuration of the telephoto lens assembly 40 provides better correction of chromatic aberrations because the positive and negative lens groups 45, 50, respectively, exhibit opposing chromatic dispersion characteristics that partially cancel each other. This chromatic correction is helpful even for nominally monochromatic ultraviolet laser illumination because the finite laser linewidth and any residual fluorescence or Raman scattering from optical components could otherwise introduce wavelength-dependent focus variations.

An objective lens 55 is positioned to receive the expanded ultraviolet laser beam 20 from the telephoto lens assembly 40 and focuses the beam 20 onto the tissue sample 60 to create a diffraction-limited focal spot. The objective lens 55 is configured as an F-theta scan lens, which is a specialized type of objective lens specifically designed for laser scanning applications. The term "F-theta lens" refers to a lens designed such that the image height (the radial distance of the focused spot from the optical axis) is proportional to the product of the effective focal length F and the scan angle theta, rather than following the natural tangent relationship that characterizes conventional lenses. Mathematically, for an F-theta lens, the image height h equals F multiplied by theta, whereas for a conventional lens, h would equal F multiplied by the tangent of theta. This linear relationship between scan angle and image position is achieved through deliberate introduction of barrel distortion that compensates for the tangent nonlinearity. The F-theta lens configuration provides unique features for the scanning photoacoustic microscopy system 10. First, it ensures that uniform angular velocity of the polygon scanner 25 translates directly into uniform linear scanning velocity at the sample plane, eliminating the velocity variations that would otherwise occur due to the tangent relationship in conventional lenses. Second, it maintains a flat field, meaning that the focal plane is flat rather than curved, allowing the entire field of view to be in focus simultaneously when imaging flat tissue surfaces. Third, it provides nearly constant spot size across the entire scan range, ensuring uniform spatial resolution throughout the image.

The focused ultraviolet laser beam 20 from the objective lens 55 illuminates the tissue sample 60, which is positioned at the focal plane of the objective lens 55. In an example, the tissue sample 60 comprises fresh, unprocessed surgical tissue that has been excised during an ongoing surgical procedure and requires rapid pathological assessment to guide surgical decision-making. The term "fresh" as used herein means tissue that has not undergone freezing, chemical fixation, dehydration, embedding, sectioning, or staining processes typically employed in conventional histopathology. The tissue sample 60 may comprise any of various tissue types including but not limited to breast tissue, bone tissue, soft tissue sarcomas, lymph nodes, brain tissue, liver tissue, kidney tissue, or other organs and tissues where intraoperative pathology assessment is clinically beneficial. When the pulsed ultraviolet laser beam 20 strikes the tissue sample 60, the ultraviolet photons are absorbed by tissue chromophores, primarily nucleic acids in cell nuclei and aromatic amino acids in proteins. This absorption converts the optical energy into heat through non-radiative relaxation processes, causing a rapid localized temperature rise in the absorbing regions. Because the laser pulse duration is in the nanosecond range and is shorter than the characteristic time for thermal diffusion and mechanical stress relaxation, the heated regions undergo rapid thermoelastic expansion. This expansion launches acoustic waves that propagate away from the heated volume as ultrasonic waves.

The system 10 includes a motorized stage 65 having at least two axes of motion 70 that enable precise three-dimensional positioning and scanning of the tissue sample 60. The motorized stage 65 comprises a multi-axis translation platform driven by stepper motors, servo motors, or linear motors capable of providing accurate and repeatable position control. The at least two axes of motion 70 include at least one axis 75 that lies in an imaging plane and an axis 80 that is orthogonal to the imaging plane. The imaging plane is defined as the plane in which the two-dimensional raster scanning pattern is executed, with the fast axis 35 (X-axis) being scanned by the polygon scanner 25 and a slow axis (Y-axis) being scanned by translation of the motorized stage 65. The axis 75 of the imaging plane, which corresponds to the Y-axis in the preferred embodiment, is scanned in a step-and-settle manner such that the motorized stage 65 incrementally translates the tissue sample 60 by a predetermined step distance after each line scan along the fast axis 35 is completed. The step distance along the Y-axis is selected to achieve the desired spatial sampling density, typically chosen to match the optical resolution along the X-axis so that the image has isotropic pixel dimensions. The axis 80 orthogonal to the imaging plane corresponds to the Z-axis or depth axis, which is perpendicular to the tissue surface and parallel to the propagation direction of the focused laser beam 20.

The motorized stage 65 is specifically configured to support the tissue sample 60 and to translate the sample along both the imaging plane axis 75 and the orthogonal axis 80 with high precision and repeatability. The stage translation along the orthogonal axis 80 is used for maintaining optimal focus when imaging tissue samples with uneven surface topography. Fresh surgical tissue specimens inherently possess irregular surface contours due to the cutting process, tissue heterogeneity, and the absence of the flattening that occurs during conventional histological processing. The height variations in these uneven surfaces frequently exceed the depth of focus of the high-numerical-aperture objective lens 55, which is typically in the range of a few to tens of micrometers for subcellular resolution imaging. If the tissue surface moves outside this shallow depth of focus due to surface height variations, the focused laser spot becomes defocused, resulting in degraded spatial resolution and reduced photoacoustic signal amplitude. The motorized stage 65 addresses this challenge by dynamically adjusting the vertical position of the tissue sample 60 along the orthogonal axis 80 during imaging to maintain the tissue surface within the optical depth of focus across the entire field of view. This dynamic focus adjustment is accomplished by vertical translation of the motorized stage 65 based on surface topography information obtained during a pre-scan procedure.

An ultrasound transducer 85 is positioned to detect photoacoustic signals 90 generated from the tissue sample 60 in response to illumination by the pulsed ultraviolet laser beam 20. The ultrasound transducer 85 comprises a piezoelectric element that converts acoustic waves into electrical voltage signals through the piezoelectric effect. The term "piezoelectric effect" refers to the generation of electric charge in response to mechanical stress in certain crystalline materials lacking a center of symmetry in their crystal structure. When acoustic waves generated by photoacoustic conversion in the tissue sample 60 impinge upon the piezoelectric element of the ultrasound transducer 85, they induce mechanical strain in the piezoelectric material. This strain causes displacement of electric charges within the crystal lattice, generating a voltage across the electrodes attached to the piezoelectric element. The amplitude and temporal characteristics of this voltage signal directly reflect the amplitude and temporal profile of the incident acoustic wave. The ultrasound transducer 85 is configured with frequency response characteristics matched to the photoacoustic signal spectrum, typically having a center frequency in the range of twenty to one hundred megahertz for subcellular resolution imaging.

Higher frequency transducers provide better spatial resolution but have shorter penetration depth due to increased ultrasonic attenuation in tissue, while lower frequency transducers provide greater penetration at the expense of resolution. The transducer bandwidth, defined as the range of frequencies over which the transducer maintains reasonable sensitivity, should be sufficiently broad to capture the harmonic content of the photoacoustic waveforms without distortion.

The photoacoustic signals 90 detected by the ultrasound transducer 85 are electrical voltage waveforms that encode spatial and absorption information about the illuminated tissue region. Each photoacoustic signal 90 corresponds to one laser pulse and originates from the tissue volume illuminated by that pulse. The temporal profile of each photoacoustic signal waveform contains depth information according to the principle of time-of-flight, whereby features in the waveform arriving at earlier times correspond to photoacoustic sources located closer to the transducer 85, while features arriving at later times correspond to deeper sources. The amplitude of features in the photoacoustic waveform reflects the optical absorption coefficient at the corresponding spatial location, with higher absorption producing larger amplitude signals. A data acquisition device 95 digitizes the photoacoustic signals 90 received from the ultrasound transducer 85, converting the analog voltage waveforms into digital numerical values suitable for computer processing and image reconstruction. The data acquisition device 95 may comprise a high-speed analog-to-digital converter (ADC) operating at sampling rates of at least 100 megasamples per second, and preferably 500 megasamples per second or higher, to adequately capture the high-frequency components of the photoacoustic waveforms without aliasing or temporal distortion.

The system 10 further comprises a controller 100 that controls the synchronized operation of all system components to enable accurate high-speed imaging. The controller 100 comprises a computational processing unit with associated memory, input/output interfaces, and control electronics capable of generating timing signals, executing control algorithms, and managing data flow throughout the system. In an example, the controller 100 is implemented using a field-programmable gate array (FPGA) that provides hardware-level parallel processing capabilities and deterministic timing control with sub-microsecond precision. The FPGA-based implementation enables the controller 100 to simultaneously manage multiple high-speed data streams and control signals without the timing jitter and latency variations that would occur in software-based control systems running on general-purpose computers. Alternatively, the controller 100 may be implemented as a combination of dedicated microcontrollers, digital signal processors, and real-time operating system software. The controller 100 interfaces with the pulsed laser source 15 through a trigger input that commands laser pulse emission, with the polygon scanner 25 through encoder signals that indicate angular position, with the motorized stage 65 through motion control commands specifying position and velocity, and with the data acquisition device 95 through sampling clock and trigger signals that define when analog-to-digital conversion should occur. The controller 100 continuously monitors the operational status of all components and adjusts control parameters in real-time to maintain optimal imaging performance.

The controller 100 controls the motorized stage 65 and is configured to perform a rapid pre-scan of the tissue sample 60 prior to acquiring high-resolution diagnostic images. This pre-scan procedure enables high-resolution imaging of tissue samples with uneven surface topography while maintaining rapid overall imaging speeds. The pre-scan is executed as a low-resolution raster scan such that the motorized stage 65 translates the tissue sample 60 through the focal region of the objective lens 55 with larger step sizes than will be used during the subsequent high-resolution imaging scan. The term "low-resolution" in this context means that the spatial sampling density is reduced compared to the high-resolution scan, with typical pre-scan pixel spacings being two to five times larger than the optical resolution of the system 10. This reduced spatial sampling allows the pre-scan to be completed rapidly, typically within ten to thirty seconds for a tissue area of several square centimeters. During the pre-scan, the controller 100 maintains the motorized stage 65 at a fixed vertical position along the orthogonal axis 80, meaning that the Z-axis position remains constant while only the X-axis and Y-axis scanning occurs. This fixed Z-position during pre-scan simplifies the scan pattern and maximizes scan speed. The faster imaging speed in the pre-scan mainly comes from the reduced spatial sampling density (downsampling). In the high-resolution scan, it is possible to scan in the X, Y, and Z axes simultaneously without pausing for vertical repositioning. Although the tissue surface may move in and out of the optimal focal plane during the pre-scan due to surface height variations, this defocusing is acceptable during the pre-scan because the goal is to extract surface topology information rather than to obtain diagnostic-quality images.

The controller 100 extracts surface topology data 105 from the photoacoustic signals 90 acquired during the pre-scan to generate a contour map 110 representing variations in surface height of the tissue sample 60. This topology extraction exploits the time-of-flight information inherently encoded in the temporal structure of each photoacoustic signal waveform. When the pulsed laser beam illuminates the tissue surface, optical absorption at the surface generates a photoacoustic wave that propagates toward the ultrasound transducer 85. The time required for this acoustic wave to travel from the tissue surface of the sample 60 to the transducer 85 is directly proportional to the distance between them, according to the relationship that distance equals ultrasound wave velocity multiplied by propagation time. In the photoacoustic signal waveform, the surface-generated signal manifests as a characteristic bipolar pulse shape consisting of a positive peak followed by a negative peak, with the time of arrival of these peaks indicating the surface depth. The controller 100 analyzes each photoacoustic waveform acquired during the pre-scan using signal processing algorithms that identify the temporal position of the surface-related features. The depth value calculated for each pre-scan pixel is stored in memory as an element of a two-dimensional array representing the surface topology.

The contour map 110 generated from the pre-scan data comprises a two-dimensional array of depth values corresponding to the surface height at each sampled position in the X-Y imaging plane. This contour map 110 mathematically represents the three-dimensional surface topography as a height function Z equals f(X,Y), where Z is the surface height above a reference plane and X, Y are the lateral coordinates in the imaging plane. The contour map 110 captures the macroscopic surface features including tissue folds, cutting artifacts, regional thickness variations, and local protrusions or depressions. Because the pre-scan spatial sampling may be coarser than the desired high-resolution image pixel spacing, the controller 100 applies interpolation algorithms to the raw pre-scan depth data to generate depth values at every high-resolution pixel location. Bilinear interpolation or bicubic interpolation methods are suitable for this purpose, creating smooth surface representations from the discrete pre-scan measurements. The interpolated contour map 110 is stored in high-speed memory accessible to the controller 100 for real-time lookup during the subsequent high-resolution imaging scan. In some embodiments, the controller 100 applies spatial filtering to the contour map 110 to remove high-frequency noise components that may have been introduced by random signal fluctuations during the pre-scan. A two-dimensional low-pass filter with a cutoff frequency corresponding to the expected spatial frequency content of real tissue surface variations effectively suppresses noise while preserving genuine surface topography.

The controller 100 synchronizes operation of the pulsed laser source 15, the polygon scanner 25, the motorized stage 65, and the data acquisition device 95 during imaging to ensure that photoacoustic signals are acquired from precisely known spatial locations. This synchronization is used for accurate image reconstruction because each digitized photoacoustic waveform is assigned to the correct pixel position in the final image. The synchronization process begins with detection of the start-of-scan timing signal that indicates when each new scan line begins. As each facet 30 of the rotating polygon scanner 25 enters the active scanning position, the deflected laser beam 20 sweeps across a start-of-scan detector positioned at the beginning of the scan trajectory. This detector generates an electrical pulse that serves as the temporal reference for that scan line. Upon receiving this start-of-scan signal, the controller 100 initiates a precisely timed sequence of laser pulses and data acquisition windows. The controller 100 sends trigger signals to the pulsed laser source 15 at regular intervals corresponding to the desired pixel spacing along the fast axis 35, causing the laser to emit pulses at positions distributed across the scan line. Simultaneously, the controller 100 triggers the data acquisition device 95 to capture the photoacoustic signals generated by each laser pulse. The timing relationship between the start-of-scan signal, laser triggers, and acquisition triggers is maintained with sub-microsecond precision to ensure accurate spatial registration. The controller 100 commands the motorized stage 65 to translate the tissue sample 60 by one step increment along the slow axis, preparing for the next scan line. This translation may occur at the completion of each scan line, or, for higher scan speed, concurrently during the fast-axis scan.

The controller 100 controls the motorized stage 65 and is configured to dynamically adjust the position of the tissue sample 60 vertically along the orthogonal axis 80 during a high-resolution imaging scan based on the contour map 110 generated from the pre-scan. This dynamic vertical adjustment maintains the tissue surface of the sample 60 within the optical depth of focus of the objective lens 55 throughout the imaging process, ensuring consistently high spatial resolution across tissue samples with irregular topography. The depth of focus (DOF), defined as the axial distance over which the focused spot size remains within an acceptable tolerance of the minimum spot size, is determined by the numerical aperture of the objective lens 55 and the wavelength of the laser light. At 266 nm excitation and submicron resolution, the depth of focus is extremely shallow, typically only on the order of a few to tens of micrometers. This shallow depth of focus necessitates precise vertical positioning to maintain optimal resolution. During the high-resolution scan, the controller 100 executes a coordinated motion pattern such that both lateral scanning (X-Y) and vertical positioning (Z) occur simultaneously. For each scan line along the fast axis 35, the controller 100 retrieves the surface height values from the contour map 110 corresponding to the pixel positions along that line. The controller 100 then instructs the motorized stage 65 to continuously adjust the Z-position as the laser beam scans along the X-axis, creating a smoothly varying vertical trajectory that tracks the tissue surface contour.

The dynamic Z-axis adjustment implemented by the controller 100 differs fundamentally from conventional approaches that attempt to adjust focus during scanning. Unlike systems that scan slowly enough to move the stage or optics vertically during each individual scan line based on real-time feedback from acquired signals, the embodiments herein use predetermined contour information from the pre-scan to enable much faster scanning speeds. By separating the topology measurement (pre-scan) from the high-resolution imaging scan, the system 10 avoids the speed limitations imposed by mechanical response time and signal processing latency. The controller 100 can command Z-axis motion based on feedforward control using the stored contour map 110, rather than feedback control that would require waiting for signal acquisition and analysis before adjusting position. This feedforward approach enables the Z-axis adjustments to be executed at high speed without waiting for sensor feedback. Furthermore, because the contour map 110 is known in advance, the controller 100 can apply motion trajectory optimization algorithms that smooth the commanded Z-position versus time profile to minimize abrupt accelerations that could induce mechanical vibrations or positioning overshoot.

FIG. 2, with reference to FIG. 1, illustrates wavelength conversion components of the photoacoustic microscopy system 10 that transform source laser light into ultraviolet laser suitable for photoacoustic excitation of cellular chromophores. The system 10 may further comprise a nonlinear crystal 115 positioned in an optical path 120 of a laser beam 125 at a first wavelength emitted by the pulsed laser source 15. The nonlinear crystal 115 functions to convert the first wavelength to a second wavelength through a nonlinear optical process known as harmonic generation. The term "nonlinear optical process" refers to optical phenomena such that the response of a material to electromagnetic radiation is not linearly proportional to the field strength, but rather depends on higher-order powers of the electric field. In an example, the nonlinear crystal 115 may be composed of cesium lithium borate ($CsLiB_6O_{10}$), which is abbreviated as CLBO, although other nonlinear materials such as beta barium borate (BBO) or lithium triborate (LBO) may be employed depending on the specific wavelength requirements and available laser characteristics.

The laser beam 125 at the first wavelength comprises pulsed laser radiation at 532 nanometers wavelength, which corresponds to green light in the visible spectrum. This 532 nm wavelength is readily produced by frequency-doubled solid-state lasers such as neodymium-doped yttrium aluminum garnet (Nd:YAG) lasers that emit at 1064 nm in the near-infrared and then undergo first-stage frequency doubling to produce 532 nm output. The pulsed laser source 15 operating at 532 nm can achieve pulse repetition frequencies of several megahertz with pulse durations in the nanosecond range. The 532 nm laser beam 125 is directed through the nonlinear crystal 115 along the optical path 120 with appropriate focusing to achieve sufficient intensity for efficient nonlinear conversion. The focusing may be accomplished using a lens positioned before the nonlinear crystal 115 that creates a beam waist inside or near the crystal where the intensity is maximized.

The nonlinear crystal 115 converts the laser beam 125 of the first wavelength to generate the ultraviolet laser beam 20 through harmonic generation, specifically second harmonic generation in the preferred embodiment. When the 532 nm laser pulses propagate through the nonlinear crystal 115, the intense electric field of the light wave drives the electrons in the crystal lattice into nonlinear oscillatory motion. These nonlinear oscillations of the electron distribution create an oscillating polarization that radiates electromagnetic waves at the second harmonic frequency, which is exactly twice the fundamental frequency. Consequently, the 532 nm fundamental wavelength is converted to 266 nm second harmonic wavelength. The efficiency of this conversion process depends on achieving phase-matching conditions within the nonlinear crystal 115. The conversion efficiency from 532 nm to 266 nm typically ranges from 10-30% percent depending on the crystal length, beam focusing conditions, and peak intensity.

FIG. 3, with reference to FIGS. 1 and 2, illustrates the start-of-scan (SOS) detection that provides precise temporal synchronization for the high-speed scanning operations. The system 10 may further comprise an optical fiber 130 having a stripped tip 135 positioned at the beginning of a scanning trajectory of the ultraviolet laser beam 20. The optical fiber 130 comprises a multimode optical fiber capable of transmitting ultraviolet wavelengths, typically constructed with a fused silica core and fluorine-doped silica cladding to provide appropriate refractive index contrast for waveguiding. The term "multimode" indicates that the fiber core diameter is large enough to support propagation of multiple transverse electromagnetic modes, typically having a core diameter in the range of fifty to two hundred micrometers. The stripped tip 135 refers to a portion of the optical fiber 130 where the protective polymer coating has been mechanically or chemically removed to expose the bare glass fiber.

The stripped tip 135 of the optical fiber 130 is positioned at the beginning of the scanning trajectory, which is the spatial location where the deflected ultraviolet laser beam 20 first enters the active scan range as each new facet 30 of the polygon scanner 25 begins its scanning period. The stripped tip 135 is oriented such that the fiber axis is approximately perpendicular to the direction of the scanning beam propagation, allowing the beam 20 to strike the cylindrical side surface of the optical fiber 130. When the ultraviolet laser beam 20 sweeps across the stripped tip 135, a portion of the light is coupled into the fiber through side illumination. The coupled light propagates along the optical fiber 130 toward the detection end where it is measured by a photodetector (comprising the optical fiber 130 and photodiode 140).

The photodiode 140 is optically coupled to the optical fiber 130 at the opposite end from the stripped tip 135. The photodiode 140 comprises a semiconductor photodetector with spectral sensitivity extending into the ultraviolet wavelength range, typically implemented using silicon photodiodes with UV-enhanced coatings or specialized wide-bandgap semiconductor materials such as silicon carbide or gallium nitride that have intrinsic ultraviolet sensitivity.

The photodiode 140 generates a start-of-scan timing signal 145 when the deflected ultraviolet laser beam 20 strikes the stripped tip 135 of the optical fiber 130. This start-of-scan timing signal 145 comprises a brief electrical pulse, typically with duration of several nanoseconds to tens of nanoseconds, occurring once per scan line as each facet 30 of the polygon scanner 25 initiates its sweep across the field of view. The timing signal 145 serves as the temporal reference point that defines the beginning of each scan line, allowing the controller 100 to precisely determine the spatial position of the laser beam throughout the subsequent scanning period. The start-of-scan timing signal 145 is electrically transmitted to the controller 100. Upon receiving the start-of-scan timing signal 145, the controller 100 initiates a sequence of precisely timed laser trigger pulses and data acquisition trigger pulses that are synchronized to the known scanning trajectory. Because the polygon scanner 25 rotates at constant angular velocity, the beam position as a function of time after the start-of-scan signal can be calculated from the scanner geometry and rotational speed. The controller 100 uses this relationship to determine when to trigger laser pulses such that they occur at the desired pixel positions along the scan line.

FIG. 4, with reference to FIGS. 1 through 3, illustrates transmission mode detection configurations such that the ultrasound transducer 85 is positioned on the opposite side of the tissue sample 60 from the optical illumination. The ultrasound transducer 85 is configured to detect the photoacoustic signals 90 in a transmission mode 150 of signal detection. The term "transmission mode" as used herein refers to a detection geometry such that ultrasonic waves generated by photoacoustic conversion in the tissue sample 60 propagate through the thickness of the sample 60 and are detected by the transducer 85 positioned on the side opposite to the laser illumination. This is in contrast to reflection mode (also called epi-detection mode) where the transducer 85 is positioned on the same side as the illumination and detects acoustic waves that propagate back toward the laser source. Moreover, transmission mode 150 may be less susceptible to acoustic impedance mismatch artifacts that can occur at the tissue surface in reflection mode. Also, transmission mode 150 may separate the optical delivery path from the acoustic detection path, allowing independent optimization of each.

In a first configuration 155 of the transmission mode 150 of signal detection, the ultrasound transducer 85 comprises a cylindrically focused transducer 160 providing a one-dimensional line focus 165 for signal detection. The cylindrically focused transducer 160 is constructed from a piezoelectric material that has been shaped into a cylindrical geometry, meaning it has curvature along one axis while being flat along the perpendicular axis. This cylindrical focusing creates an acoustic focal zone that is elongated along one direction, forming a line focus rather than a point focus. The term "one-dimensional line focus" refers to this elongated focal region where acoustic sensitivity is maximized, having high spatial resolution along one axis (the focusing direction) while having extended sensitivity along the perpendicular axis (the non-focusing direction). The cylindrically focused transducer 160 is typically fabricated by hot-pressing or mechanically shaping a flat piezoelectric element into the desired cylindrical radius of curvature. The cylindrical radius is selected to achieve the desired focal distance, which should match the position of the tissue sample 60, and the desired focal zone dimensions.

The ultraviolet laser beam 20 is confocal with the one-dimensional line focus 165 and is scanned along the one-dimensional (1D) line focus 165 during imaging operations. The term "confocal" in this context means that the optical focus of the laser beam 20 coincides spatially with the acoustic 1D line focus 165 of the ultrasound transducer 160, ensuring maximum detection sensitivity for photoacoustic signals generated at the laser focal spot. This confocal arrangement is achieved through careful alignment of the relative positions and orientations of the objective lens 55 and the cylindrically focused transducer 160. The laser beam 20 is focused to a spot on the tissue surface of the sample 60 that lies along the acoustic 1D line focus 165, and as the polygon scanner 25 deflects the beam along the fast axis 35, the optical focal spot scans along the length of the acoustic 1D line focus 165. This scanning geometry ensures that throughout the entire scan line, the laser-illuminated region remains within the zone of maximum acoustic sensitivity of the transducer. The elongated nature of the 1D line focus 165 maintains high detection sensitivity across the entire scan range without requiring the transducer 160 to be mechanically scanned or repositioned. The length of the 1D line focus 165 is configured to be equal to or greater than the maximum scan range along the fast axis 35, ensuring complete coverage of the field of view.

The confocal line-scanning geometry of the first configuration 155 provides superior signal-to-noise ratio compared to alternative detection schemes. Because the acoustic sensitivity is concentrated along the focal line 165 where the laser scanning occurs, photoacoustic signals generated within this focal zone are detected with maximum efficiency while acoustic noise originating from outside the focal zone is naturally suppressed by the acoustic focusing characteristics. This spatial selectivity improves image contrast by reducing background signals from out-of-focus regions. The single-element nature of the cylindrically focused transducer 160 also enables simple single-channel signal acquisition without requiring multiple parallel acquisition channels or complex beamforming algorithms, reducing system cost and complexity while enabling real-time image display as scan lines are acquired.

In a second configuration 180 of the transmission mode 150 of signal detection, the ultrasound transducer 85 is arranged as a linear ultrasound transducer array 185 comprising multiple individual transducer elements 190 arranged along a line. Each transducer element 190 in the array 185 comprises an independent piezoelectric element with its own electrical connections, allowing signals to be acquired from each element separately. The linear array 185 is positioned such that its elements are distributed along the fast scanning axis 35. During scanning, as the laser beam 20 sweeps along the fast axis 35, it sequentially illuminates different positions along the tissue sample 60. The transducer elements 190 detect signals 195 from a illuminated spot 200 on the tissue sample 60. The transducer element 190 positioned closest to the illuminated spot 200 receives the strongest signal because the acoustic wave propagates directly toward it along the shortest path, while neighboring elements receive weaker signals due to the greater propagation distance and angular dependence of acoustic radiation patterns.

The parallel detection capability of the array 185 improves signal to noise ratio (SNR) through spatial sampling of the acoustic aperture. A lightweight reconstruction step is applied in which the known illumination position (derived from scan timing and SOS reference) is used to determine the spatial location of each detected signal. This approach does not require full beamforming or time-reversal algorithms, but still provides fast reconstruction with minimal latency suitable for real-time display. The linear array 185 also provides flexibility for implementing advanced signal processing techniques such as coherent averaging across neighboring elements to improve SNR, or differential detection schemes where signals from adjacent elements are subtracted to enhance edge detection.

Figure 5:
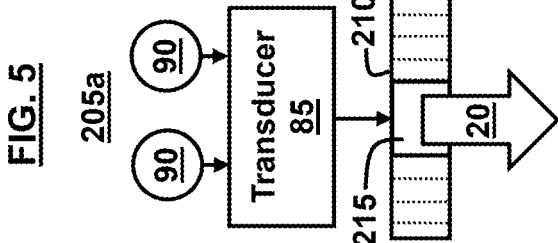
FIG. 5 is a block diagram illustrating a reflection mode detection configuration using a cylindrically focused transducer with a slit aperture, according to an embodiment herein.

FIG. 5, with reference to FIGS. 1 through 4, illustrates a reflection mode detection configuration 205a where both optical excitation and acoustic detection occur from the same side of the tissue sample 60. The ultrasound transducer 85 is configured to detect photoacoustic signals 90 in a reflection mode 205a of signal detection. In reflection mode 205a, photoacoustic waves generated within the tissue propagate upward toward the tissue surface and are detected by a transducer 85 positioned above the sample 60 on the same side as the laser illumination. Reflection mode 205a detection may be used for thick tissue specimens where transmission through the entire sample thickness would result in excessive acoustic attenuation, and for clinical applications where only single-sided access to the tissue is available. The reflection mode 205a configuration illustrated in FIG. 5 employs a specialized transducer configuration that permits coaxial transmission of the excitation laser beam while maintaining efficient acoustic detection capability.

The ultrasound transducer 85 in this reflection mode configuration 205a comprises a cylindrically focused transducer element 210 having a central rectangular slit aperture 215 that permits coaxial transmission of the ultraviolet laser beam 20 therethrough. The cylindrically focused transducer element 210 is fabricated from a piezoelectric material such as lithium niobate (LNO) that has been shaped to have cylindrical curvature for one-dimensional acoustic focusing, similar to the transmission mode cylindrical transducer described previously. However, this reflection mode transducer element 210 includes the additional feature of the central rectangular slit aperture 215, which is a narrow opening cut through the piezoelectric material along the length of the cylinder axis. The slit aperture 215 has dimensions selected to allow unobstructed passage of the scanning laser beam 20 while minimizing the reduction in active transducer area. Example slit dimensions might be one to three millimeters in width along the focusing direction and ten to twenty millimeters in length along the cylindrical axis direction. The slit aperture 215 is precisely positioned at the center of the transducer element 210, aligned with the optical axis of the focusing system, such that the laser beam 20 passes through the slit aperture 215 and reaches the tissue sample 60 without striking the piezoelectric material.

The geometry of the slit aperture 215 enables truly coaxial optical delivery and acoustic detection, meaning the laser beam and acoustic waves share the same propagation axis with the laser beam traveling downward through the slit aperture 215 and acoustic waves propagating upward from the tissue to the transducer 85. This coaxial arrangement provides optimal geometric efficiency because photoacoustic signals generated at the tissue surface directly beneath the laser focal spot propagate straight upward to the transducer without angular deviation. In an example, the cylindrically focused transducer element 210 is an intact single-piece structure with a slit aperture 215 passing through the central region of the element. The cylindrical focusing of the transducer element 210 concentrates acoustic sensitivity to a one-dimensional focal line located at the tissue surface, just as in the transmission mode cylindrical transducer configuration. The laser focal spot is scanned along this acoustic focal line to maintain confocal alignment throughout the scan range.

The transducer element 210 may be fabricated from lithium niobate (LiNbO$_3$), which has an exceptionally high piezoelectric coefficient and favorable electrical impedance characteristics that enable efficient conversion of acoustic pressure into electrical signals. The transducer structure includes acoustic matching layers positioned between the piezoelectric element 210 and the water or coupling medium through which acoustic waves propagate. These acoustic matching layers comprise materials with acoustic impedance values intermediate between the high impedance of lithium niobate (approximately 34 megarayls) and the low impedance of water (1.5 megarayls). By providing gradual impedance transition, the matching layers reduce acoustic reflection losses at the transducer interface and increase the transmitted acoustic energy into the piezoelectric element.

A backing layer (not shown) is attached to the rear surface of the piezoelectric element 210 opposite to the acoustic receiving surface. In some implementations, the backing layer comprises a high-attenuation material (e.g., epoxy composite filled with tungsten powder or other high-density particles), but other backing materials or structures may also be used depending on desired bandwidth and sensitivity. The backing layer serves to dampen acoustic reverberations within the piezoelectric element that would otherwise persist after the initial acoustic pulse, causing temporal ringing that degrades the temporal resolution of the transducer. By absorbing acoustic energy that propagates rearward from the piezoelectric element, the backing layer shortens the impulse response duration and increases the bandwidth of the transducer frequency response. A thin Parylene-C coating may be applied to the exterior surface (and in some embodiments, other biocompatible conformal barrier coatings may be used instead). Parylene-C is a biocompatible polymer that can be deposited as a conformal coating through chemical vapor deposition, creating a pinhole-free protective layer with precisely controlled thickness. This Parylene-C coating serves dual functions: first, it provides physical and chemical protection for the acoustic matching layers and piezoelectric material against water ingress and chemical degradation; second, its acoustic impedance (approximately 2.5 megarayls) functions as an additional acoustic matching layer that further optimizes the impedance transition between water and the underlying matching layer stack.

The acoustic stack comprising the matching layers, piezoelectric element, and backing layer is formed into a cylindrical geometry through hot-pressing or precision machining processes to ensure uniform sensitivity and signal detection performance across the entire scan line. The cylindrical radius of curvature is selected based on the desired focal distance and focal zone characteristics.

Figure 6:
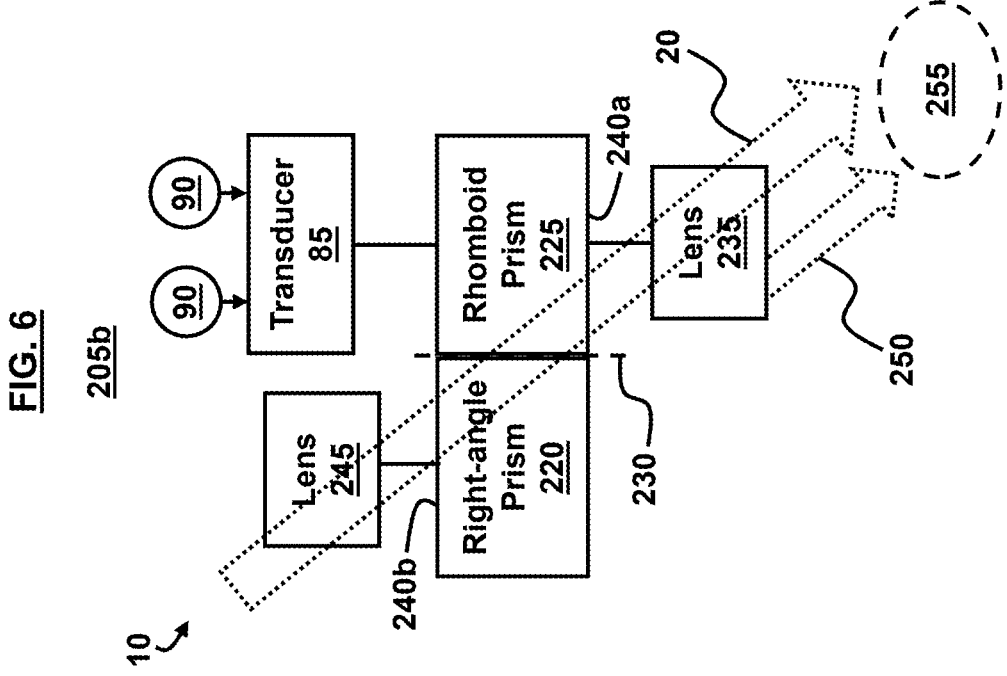
FIG. 6 is a block diagram illustrating a reflection mode detection configuration using a prism-based ultrasound transducer assembly, according to an embodiment herein.

FIG. 6, with reference to FIGS. 1 through 5, illustrates an alternative reflection mode detection configuration 205b that achieves optical and acoustic confocality through a prism-based coupling assembly rather than a slit-aperture transducer. According to an example, in a reflection-mode signal detection approach, the system 10 may further comprise a right-angle prism 220 and a rhomboid prism 225 separated by an optical coupling medium 230. This two-prism configuration provides a solution to the challenge of achieving coaxial optical delivery and acoustic detection without requiring a physical aperture in the transducer element. The right-angle prism 220 comprises an optical element with a triangular cross-section having one right angle and two 45° angles. The prism 220 is fabricated from an optically transparent material such as fused silica that has high transmission at ultraviolet wavelengths. The rhomboid prism 225 comprises a four-sided prism with parallelogram cross-section, typically having opposite face angles of 45°. The rhomboid prism 225 is fabricated from a material suitable for both optical transmission and acoustic propagation, such as fused silica.

The optical coupling medium 230 separating the right-angle prism 220 and rhomboid prism 225 comprises a thin layer of liquid couplant. Silicone oil is the preferred coupling medium because it offers excellent transmission of ultraviolet light and provides a solid-liquid impedance boundary for reflection of ultrasonic waves while remaining stable against evaporation and chemical degradation. The ultrasound transducer 85 is mounted on the upper surface of the rhomboid prism 225 and acoustically coupled thereto through an additional acoustic coupling medium (such as ultrasound gel, glycerol, and castor oil). This transducer mounting configuration allows the transducer to detect acoustic waves that have propagated through the tissue sample 60 and through the prism structure.

The rhomboid prism 225 includes an acoustic cylindrical lens 235 ground into a surface 240a thereof, specifically the bottom surface that faces toward the tissue sample 60. The acoustic cylindrical lens 235 is created by machining the bottom surface of the rhomboid prism 225 into a cylindrical concave shape that acts as a focusing element for incoming acoustic waves. As photoacoustic waves generated in the tissue propagate upward through the water (or coupling medium) and enter the fused-silica prism, they refract at the curved water-silica interface according to Snell's law for acoustic waves. The cylindrical curvature is chosen so that these refracted waves converge within the prism, directing energy toward the ultrasound transducer mounted on the prism. This creates an elongated detection zone analogous to that produced by a cylindrically focused receiving transducer.

The right-angle prism 220 includes an optical correction lens 245 ground on a top surface 240b thereof to compensate for optical aberrations introduced by the acoustic cylindrical lens 235 on the rhomboid prism 225. When the ultraviolet laser beam 20 passes through the curved bottom surface of the rhomboid prism 225 that forms the acoustic cylindrical lens 235, the cylindrical curvature acts as a cylindrical optical lens due to the refractive index difference between fused silica and the water or coupling medium 230. This optical lensing effect, while beneficial for acoustic focusing, would introduce undesirable cylindrical aberration and astigmatism into the focused laser spot if left uncorrected. The optical correction lens 245 is designed with a cylindrical curvature that exactly compensates for the optical power of the acoustic lens 235, resulting in a net zero optical effect so that the laser beam focuses to a diffraction-limited circular spot rather than an elongated elliptical spot.

The ultrasound transducer 85 is mounted on the upper surface of the rhomboid prism 225 and acoustically coupled thereto through a thin layer of acoustic couplant. This mounting configuration positions the transducer 85 above the prism structure where it can detect acoustic waves that have propagated upward from the tissue sample 60 through the water or coupling medium, through the rhomboid prism 225, and into the transducer 85. The transducer 85 comprises a flat piezoelectric element, which may be fabricated from lithium niobate or lead zirconate titanate, with electrodes (not shown) on its top and bottom surfaces. When acoustic waves reach the transducer element, they cause mechanical strain that generates electrical charge through the piezoelectric effect, creating a voltage signal between the electrodes.

The right-angle prism 220 and the rhomboid prism 225 guide the ultraviolet laser beam 20 and acoustic waves 250 to a common focal region 255 through a sequence of refractions and reflections. The ultraviolet laser beam 20 enters the right-angle prism 220 through one of its perpendicular faces, passes through the optical correction lens 245 on the top surface where it receives compensating cylindrical optical power, then exits through at approximately 45°. The beam 20 then crosses the thin silicone oil coupling medium 230 and enters the rhomboid prism 225 through its upper angled surface. Inside the rhomboid prism 225, the beam 20 propagates downward and exits through the bottom surface where the acoustic cylindrical lens 235 is located. As the beam 20 exits into the water or coupling medium below the prism, it is refracted and focused toward the tissue sample 60, creating the focal region 255. Simultaneously, acoustic waves 250 generated by photoacoustic conversion in the tissue at the focal region 255 propagate upward through the water and enter the rhomboid prism 225 through the curved bottom surface of the acoustic lens 235. The cylindrical curvature refracts these acoustic waves, causing them to converge as they propagate upward through the prism toward the transducer mounted on the top surface.

The upward-propagating longitudinal acoustic waves undergo two reflections and associated mode conversions within the rhomboid prism 225. At the first reflection, which occurs at a solid-liquid interface at an oblique incidence angle (approximately 45°), a majority of the longitudinal wave energy converts into shear waves based on Snell's law and the acoustic boundary conditions. At the subsequent reflection from a solid-air interface at similar angles, the shear-wave energy is reconverted back into longitudinal waves with very high efficiency (~97.2%)

Moreover, because the ultrasound transducer exhibits much greater sensitivity to longitudinal waves than to shear waves due to the polarization direction of its piezoelectric response, this shear-to-longitudinal reconversion concentrates acoustic energy into the detectable wave mode. Theoretical calculations based on acoustic transmission coefficients and mode conversion efficiencies indicate that this multi-step reflection and conversion process can increase the detected longitudinal wave energy by up to approximately 20 dB compared to conventional configurations that employ simple direct propagation paths. The 20 dB improvement corresponds to a factor of ten increase in detected acoustic pressure amplitude, which translates to a hundredfold improvement in signal power, dramatically enhancing the signal-to-noise ratio and enabling detection of weaker photoacoustic signals from deeper tissue regions or from weakly absorbing structures.

During imaging operations with the prism-based transducer configuration, the acoustic focal line created by the acoustic cylindrical lens 235 defines the one-dimensional detection region where acoustic sensitivity is maximized. The excitation laser beam 20 is rapidly scanned along this acoustic focal line using the polygon scanner 25, creating the same type of confocal line-scanning geometry described for the transmission mode cylindrical transducer. This approach integrates single-spot optical excitation with one-dimensional line detection of photoacoustic signals, providing high detection efficiency across the entire scan range. The acoustic cylindrical lens 235 and the entire prism assembly are immersed in a water tank to ensure proper acoustic coupling between all optical and acoustic components. A transparent window (not shown) is provided at the bottom of the water tank (not shown in FIG. 6), sealed with a thin polyethylene membrane that is acoustically and optically transparent, allowing both the laser beam 20 and photoacoustic signals 90 to pass through with minimal attenuation or distortion. The polyethylene membrane thickness is typically selected to be 25-50 μm, thin enough to avoid significant acoustic impedance mismatch while being mechanically robust enough to contain the coupling water.

The prism-based transducer configuration provides several important advantages over other detection geometries. Unlike multi-focus photoacoustic microscopy systems that require transducer arrays with dozens or hundreds of individual elements and correspondingly complex multi-channel data acquisition hardware, the prism-based system using a single-element transducer enables simple single-channel data acquisition. This single-channel approach eliminates the need for computationally intensive reconstruction algorithms that would be required to form coherent images from signals detected by multiple array elements at different positions and times. The ability to provide real-time visualization of imaging results without post-processing delays is particularly valuable for intraoperative applications where immediate feedback is essential for surgical decision-making. Another feature of the system 10 is the ability to accommodate samples 60 with uneven surfaces through dynamic Z-axis position adjustment. Because only a single focal spot 200 is illuminated at any given time and detection occurs along a one-dimensional line rather than requiring all foci to lie in a common plane, the system 10 can continuously adjust the sample vertical position to compensate surface height variations for maintaining high resolution. This capability is not feasible in multi-focus systems where all illuminated spots must remain simultaneously in focus, limiting their applicability to flat samples.

Figure 7:
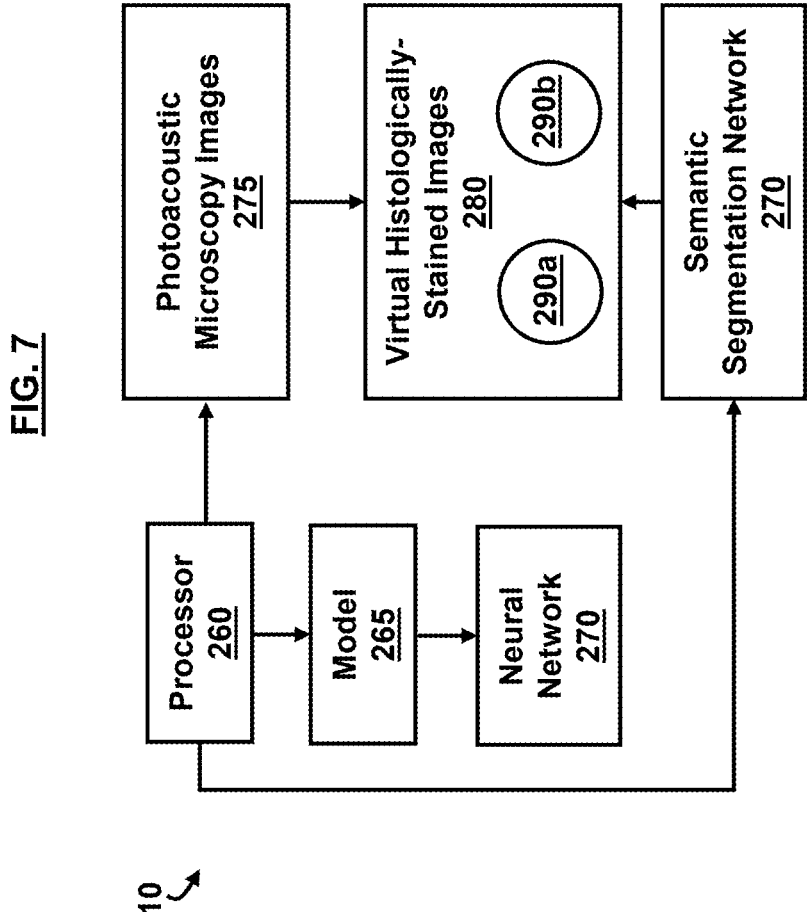
FIG. 7 is a block diagram illustrating artificial intelligence components including a conditional diffusion model and semantic segmentation network for virtual staining and margin detection, according to an embodiment herein.

FIG. 7, with reference to FIGS. 1 through 6, illustrates artificial intelligence components that extend the capabilities of the photoacoustic microscopy system 10 by transforming raw photoacoustic images 275 into virtual histologically-stained images 280 and automatically detecting tumor margins. The system 10 may further comprise a processor 260 that executes a conditional diffusion model 265 comprising a neural network 270. The processor 260 receives photoacoustic microscopy images 275 acquired using ultraviolet laser excitation as described above, and transforms these images 275 into virtual histologically-stained images 280 that simulate the appearance of conventional hematoxylin and eosin (H&E) stained tissue sections. The term "virtual staining" as used herein refers to the computational generation of synthetic histological stain appearances from label-free imaging modalities, producing images that replicate the color, contrast, and morphological features of chemically stained tissue without physically applying any stains. This virtual staining capability is particularly valuable for intraoperative pathology because it provides pathologists with images in the familiar H&E format they are trained to interpret, while avoiding the time-consuming chemical staining process that would be impractical during surgery.

The conditional diffusion model 265 implements a sophisticated generative modeling approach based on diffusion probabilistic models that have recently emerged as state-of-the-art techniques for image-to-image translation tasks in medical imaging. The fundamental principle of diffusion models involves learning to reverse a gradual noising process that progressively corrupts images with Gaussian noise. During training, the model observes paired examples of photoacoustic microscopy images 275 and corresponding histologically-stained images 280, learning how to map from the photoacoustic domain to the histological domain. The model architecture comprises the neural network 270, which may be implemented as a U-Net architecture with encoder and decoder pathways connected by skip connections. The encoder pathway progressively downsamples the input image while extracting hierarchical features at multiple scales, capturing both fine-grained details like nuclear boundaries and larger-scale structural patterns like tissue architecture. The decoder pathway upsamples these features back to the original image resolution while incorporating information from the skip connections that preserve spatial details. The term "conditional" in conditional diffusion model indicates that the generative process is conditioned on the input photoacoustic image, ensuring that the output virtual stain maintains correspondence with the structural features present in the input.

The neural network 270 is configured to enhance performance for this specific medical imaging application. Time-step embeddings are included to inform the network about the current position in the diffusion process, allowing it to adjust its behavior based on the noise level. These embeddings may be implemented as sinusoidal position encodings that are injected into the network at multiple layers. Attention mechanisms are incorporated to enable the network to focus on relevant spatial regions and feature relationships, improving its ability to accurately reproduce fine morphological details like chromatin texture within cell nuclei. The network is trained using a multi-term loss function that balances several objectives simultaneously. Reconstruction loss, typically implemented as L1 or L2 distance between generated and ground truth images, ensures basic fidelity. Perceptual loss, calculated using features extracted from a pretrained convolutional neural network such as VGG, encourages the generated images to have similar high-level perceptual characteristics to real histology. Adversarial loss from a discriminator network can be optionally included to improve realism. Structural preservation losses including structural similarity index measure (SSIM) ensure that morphological features are accurately preserved. The training process utilizes paired datasets of photoacoustic and histological images, ideally obtained from the same tissue specimens with careful spatial registration to establish pixel-level correspondence.

The processor 260 may execute a semantic segmentation network 285 to identify tumor regions 290a and non-tumor regions 290b in the virtual histologically-stained images 280. The semantic segmentation network 285 implements pixel-wise classification such that each pixel in the input image is assigned a class label indicating whether it belongs to tumor tissue or non-tumor tissue. This automated tumor margin detection provides decision support for surgeons during intraoperative procedures, enabling rapid assessment of whether surgical margins are clear of tumor or whether additional tissue removal is necessary. The semantic segmentation network 285 is typically implemented using advanced deep learning architectures such as U-Net, Deep-Labv3+, or transformer-based models that have demonstrated excellent performance on medical image segmentation tasks. The network 285 receives as input the virtual histologically-stained images 280 generated by the conditional diffusion model 265, and may also receive the original photoacoustic microscopy images 275 as additional input channels to leverage complementary information from both modalities. The photoacoustic images contain absorption-based contrast that may reveal features not equally apparent in the virtual H&E appearance, such as variations in nuclear density or protein concentration that correlate with malignancy.

The semantic segmentation network 285 architecture incorporates multi-scale feature extraction capabilities to capture morphological patterns at different spatial scales ranging from individual cell characteristics to tissue-level architectural features. Encoder layers progressively downsample the input images while extracting increasingly abstract features through convolutional operations, pooling, and nonlinear activations. Decoder layers upsample these features back to the original image resolution while combining information from multiple scales through skip connections or feature pyramid structures. Attention mechanisms, including spatial attention and channel attention modules, enable the network to dynamically focus on diagnostically relevant regions and feature channels. The network outputs a probability map such that each pixel is assigned a value between zero and one indicating the probability that the pixel belongs to tumor tissue. Thresholding this probability map at an appropriate threshold value produces a binary segmentation mask clearly delineating tumor regions 290a and non-tumor regions 290b.

The semantic segmentation network 285 is trained using annotated datasets comprising histological images with pixel-level tumor annotations created by expert pathologists. The training process employs specialized loss functions designed for segmentation tasks, including Dice loss which directly optimizes the overlap between predicted and ground truth segmentation masks. Dice loss is calculated as one minus twice the intersection of predicted and true positive pixels divided by the sum of predicted positive and true positive pixels, providing a differentiable objective that handles class imbalance between tumor and non-tumor regions. Cross-entropy loss is combined with Dice loss to provide additional gradient signal, especially during early training when predictions may be far from optimal. Boundary-aware regularization terms are incorporated to encourage accurate delineation of tumor margins, which is particularly important for surgical applications where precise margin assessment directly impacts clinical outcomes. These boundary terms apply higher weight to pixels near tumor boundaries, penalizing errors in these regions more heavily than errors in tissue interiors. Data augmentation strategies including geometric transformations such as rotation, flipping, and elastic deformation, as well as color jittering and simulated noise, improve the network's ability to generalize across diverse tissue types, scanning conditions, and biological variations.

In some examples, the processor 260 described herein and/or illustrated in the figures may be embodied as hardware-enabled modules and may be configured as a plurality of overlapping or independent electronic circuits, devices, and discrete elements packaged onto a circuit board to provide data and signal processing functionality within a computer. An example might be a RF switch, antenna tuner, comparator, inverter, or flip-flop, which could include a plurality of transistors and other supporting devices and circuit elements. The modules that are configured with electronic circuits process and/or execute computer logic instructions capable of providing digital and/or analog signals for performing various functions as described herein including controlling the operations of the system 10 and associated components. In some examples, the processor 260 may comprise a central processing unit (CPU) of the system 10. In other examples the processor 260 may be a discrete component independent of other processing components in the system 10. In other examples, the processor 260 may be a semiconductor-based microprocessor, micro-controller, field-programmable gate array (FPGA), hardware engine, hardware pipeline, and/or other hardware-enabled device suitable for receiving, processing, operating, and performing various functions for the system 10. The processor 260 may be provided in the system 10, coupled to the system 10, or communicatively linked to the system 10 from a remote networked location, according to various examples.

Furthermore, in some examples, the system 10 may comprise various controllers, switches, processors, and circuits, which may be embodied as hardware-enabled modules and may be a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that include electronic circuits process computer logic instructions capable of providing digital and/or analog signals for performing various functions as described herein. The various functions can further be embodied and physically saved as any of data structures, data paths, data objects, data object models, object files, database components. For example, the data objects could include a digital packet of structured data. Example data structures may include any of an array, tuple, map, union, variant, set, graph, tree, node, and an object, which may be stored and retrieved by computer memory and may be managed by processors, compilers, and other computer hardware components. The data paths can be part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be physical locations in computer memory and can be a variable, a data structure, or a function. Some examples of the modules include relational databases (e.g., such as Oracle® relational databases), and the data objects can be a table or column, for example. Other examples include objects, distributed objects, object-oriented programming objects, and semantic web objects. The data object models can be an application programming interface for creating HyperText Markup Language (HTML) and Extensible Markup Language (XML) electronic documents. The models can be any of a tree, graph, container, list, map, queue, set, stack, and variations thereof, according to some examples. The data object files can be created by compilers and assemblers and contain generated binary code and data for a source file. The database components can include any of tables, indexes, views, stored procedures, and triggers.

Figure 8:
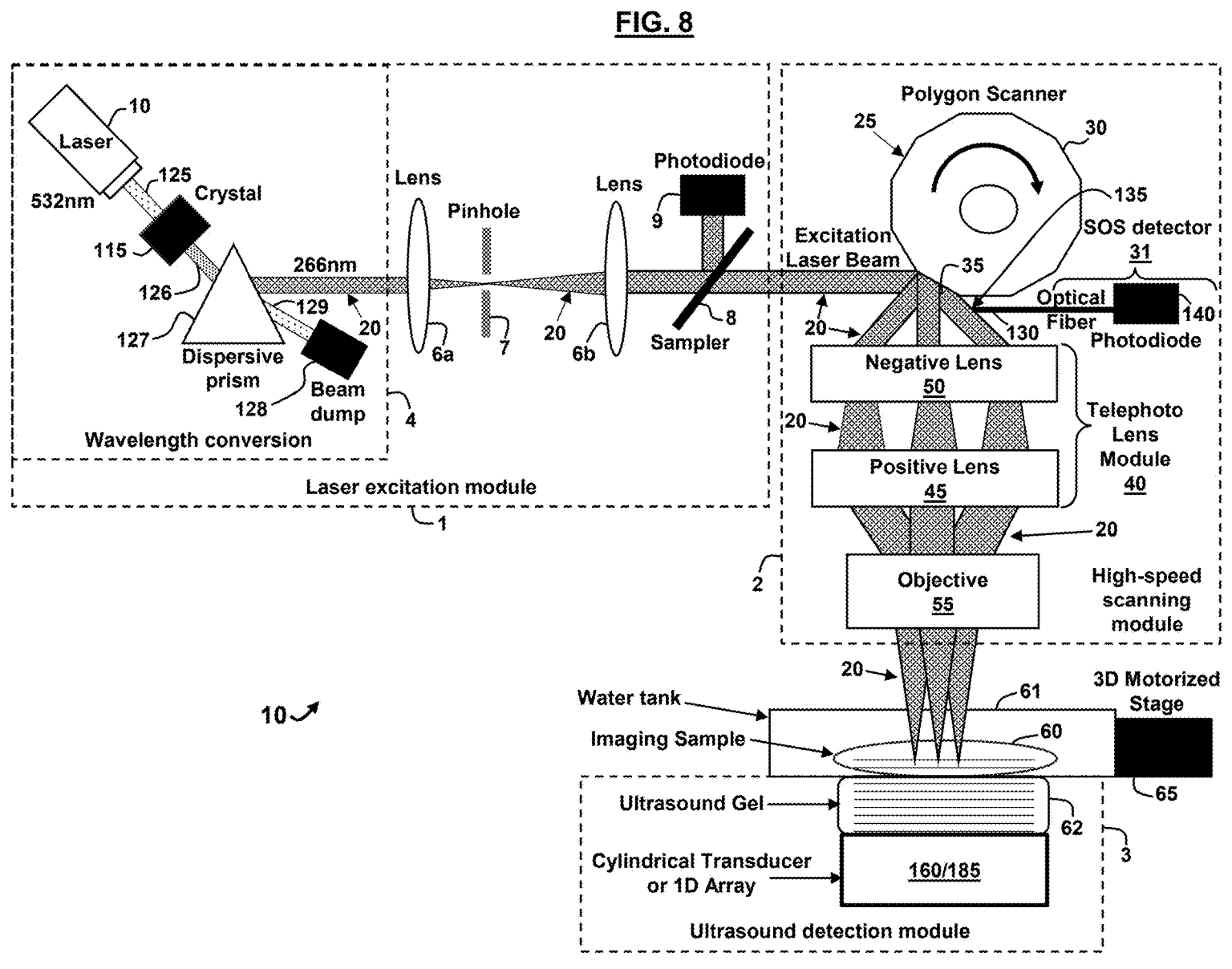

FIG. 8, with reference to FIGS. 1 through 7, is a schematic block diagram illustrating the system 10 as an optically coupled arrangement of modules including a laser excitation module 1, a high-speed scanning module 2, and an ultra-sound detection module 3. The laser excitation module 1 comprises a laser system 4, which provides for wavelength conversion of a laser beam 20. The laser excitation module 1 begins with a high-repetition-rate pulsed laser 11 that serves as the primary excitation source for the photoacoustic microscopy system 10. This laser 11 emits pulses at a wavelength of 532 nanometers, which appears as green light in the visible spectrum. The high repetition rate, typically operating at several megahertz, is used for achieving the rapid imaging speeds for intraoperative pathology applications. Each laser pulse contains sufficient energy to generate photoacoustic signals when absorbed by a tissue sample 60, yet the pulse duration is short enough to create the transient thermal expansion needed for efficient acoustic wave generation.

The 532 nm laser beam 125 is directed into a nonlinear crystal 115, which can be made of any suitable material (e.g., cesium lithium borate (CLBO), according to an example), where a second harmonic generation 126 transforms the wavelength of the beam 125. As the high-intensity laser light passes through the crystal 115, the nonlinear optical properties of the material cause two photons at 532 nm to combine and generate a single photon at exactly half the wavelength (266 nm), which falls in the ultraviolet spectrum. This wavelength conversion process is highly dependent on phase-matching conditions within the crystal 115, which is why the beam 125 is properly focused through the crystal 115 to achieve efficient conversion. The resulting output from the crystal 115 is a mixture of both the newly generated 266 nm ultraviolet light (e.g., laser beam 20) and residual unconverted 532 nm light. The 266 nm wavelength is specifically targeted because it coincides with the strong absorption peaks of nucleic acids (DNA and RNA) and proteins in biological tissue, enabling high-contrast, label-free imaging of cellular structures that are for pathological assessment.

After emerging from the nonlinear crystal 115, the mixed-wavelength beam encounters a dispersive prism 127 that serves as a wavelength separator to purify the ultraviolet output. The dispersive prism 127 utilizes the wavelength-dependent refraction of light, bending the 266 nm ultraviolet beam 20 and the 532 nm green beam at different angles as they pass through the prism 127. This angular separation allows the module 1 to cleanly divide the two wavelengths spatially. The unwanted 532 nm residual light 129, which did not undergo conversion in the crystal 115, is directed toward a beam dump 128, which is an optical absorber configured to safely dissipate this excess light energy without reflection or scatter that could contaminate the optical path. Meanwhile, the desired 266 nm ultraviolet beam 20 continues along the primary optical axis toward subsequent beam conditioning components. This wavelength purification step is helpful because any residual 532 nm light reaching the tissue sample 60 could generate photoacoustic signals at the wrong contrast mechanism, degrading the nuclear and protein specificity that makes ultraviolet photoacoustic microscopy effective for pathology imaging.

The ultraviolet beam 20 then passes through the first of two plano-convex lenses 6a, 6b that together form a beam expander system. This first lens 6a is positioned to receive the relatively narrow collimated beam 20 from the upstream wavelength conversion components and begins the process of controlled beam expansion. The lens 6a focuses the beam 20 to create a diverging wavefront that causes the beam diameter to increase as it propagates forward. A pinhole 7 is positioned at the focal point of the expanding beam 20. As the ultraviolet light converges through the pinhole 7, the aperture selectively transmits only the central, highest-quality portion of the beam 20 while blocking peripheral rays that contain aberrations, diffraction artifacts, or intensity irregularities. The pinhole 7 effectively filters the beam 20 by removing spatial frequency components that would degrade image quality.

Following spatial filtering, the diverging ultraviolet beam 20 encounters the second plano-convex lens 6b positioned to re-collimate and prepare the beam 20 for scanning. This lens 6b captures the expanding wavefront emerging from the pinhole 7 and transforms it back into a parallel beam, but now with a larger diameter than the original input beam. The purified 266 nm ultraviolet beam 20 next encounters a UV-fused silica beam sampler 8, which may be configured as a partially reflective optical element that extracts a small fraction of the beam for real-time energy monitoring. The beam sampler 8 is configured to reflect approximately 4-10% of the incident light at a specific angle while transmitting the remaining 90-96% to continue along the main optical path. The reflected sample beam 20 is directed onto a silicon photodiode 9. For example, the photodiode 9 may be a fast photodetector that converts the optical pulse energy into an electrical signal proportional to the instantaneous laser power. This photodiode 9 continuously monitors every laser pulse, providing feedback about pulse-to-pulse energy fluctuations that may occur in the system 10. The electrical signal from the photodiode 9 is sent to a data acquisition device 95 (shown in FIG. 12), which uses these measurements to normalize the photoacoustic signal amplitudes during image reconstruction. Without this energy normalization, variations in laser pulse energy would appear as intensity artifacts in the final pathology images, potentially leading to misdiagnosis. The main ultraviolet beam 20, having lost only a small fraction of its energy to the beam sampler 8, continues forward with sufficient power for tissue excitation.

The high-speed scanning module 2 operates by directing the ultraviolet laser beam 20 onto the rotating polygon scanner 25, which comprises multiple reflective facets 30 that sequentially deflect the beam 20 along the fast-scanning axis 35. As each new facet 30 rotates into position, the beam 20 sweeps across a start-of-scan (SOS) detector 31 positioned at the beginning of the scanning trajectory. The SOS detector 31 comprises the optical fiber 130 with a stripped tip 135 that captures the incoming laser light when the beam 20 enters the scan range, and the photodiode 140 is optically coupled to the optical fiber 130 that converts this light into an electrical timing signal. The deflected beam 20 then passes through the telephoto lens module 40, which comprises a positive lens 45 and a negative lens 50 arranged in a telephoto configuration that expands the beam while compressing its angular divergence, thereby filling the rear aperture of the objective lens 55 to maximize numerical aperture and maintain consistent resolution across the scanning field.

After expansion by the telephoto lens module 40, the objective lens 55 focuses the scanning beam 20 onto the surface of the tissue sample 60, creating a tightly focused spot that scans rapidly along the fast axis as the polygon scanner 25 rotates. The motorized sample stage 65 translates the sample 60 along the slow axis perpendicular to the laser scanning direction, converting each fast-axis scan line into a complete two-dimensional raster image. The combination of ultra-fast scanning from the polygon scanner 25 for the X-axis, precise SOS detection 130, 135, 140 for timing synchronization, telephoto beam conditioning 40, 45, 50 for resolution preservation, and motorized stage 65 translation for the Y-axis enables rapid acquisition of high-resolution photoacoustic pathology images across the specimen 60.

In FIG. 8, the ultrasound detection module 3 operates in transmission mode, where the excitation laser beam 20 illuminates the tissue sample 60 from above while photoacoustic signals are detected on the opposite side by a cylindrical transducer or 1D array 85. In the first configuration, the cylindrical transducer 85 provides a one-dimensional line focus for signal detection, with the optical focus of the scanning laser beam 20 maintained confocal with this acoustic line focus to maximize detection sensitivity. In the second configuration, a linear 1D transducer array 85 enables direct spatial mapping between scanning position and detector elements without requiring complex image reconstruction algorithms. The water tank 61 serves dual functions by providing optical coupling to transmit the focused ultraviolet beam 20 to the tissue surface without air-gap reflections that would degrade focus quality, and it acts as an acoustic impedance-matching medium that enables efficient propagation of photoacoustic waves from the tissue specimen downward through the ultrasound gel 62 to the transducer 85, preventing the severe signal loss that could occur at tissue-air interfaces.

Figure 9:
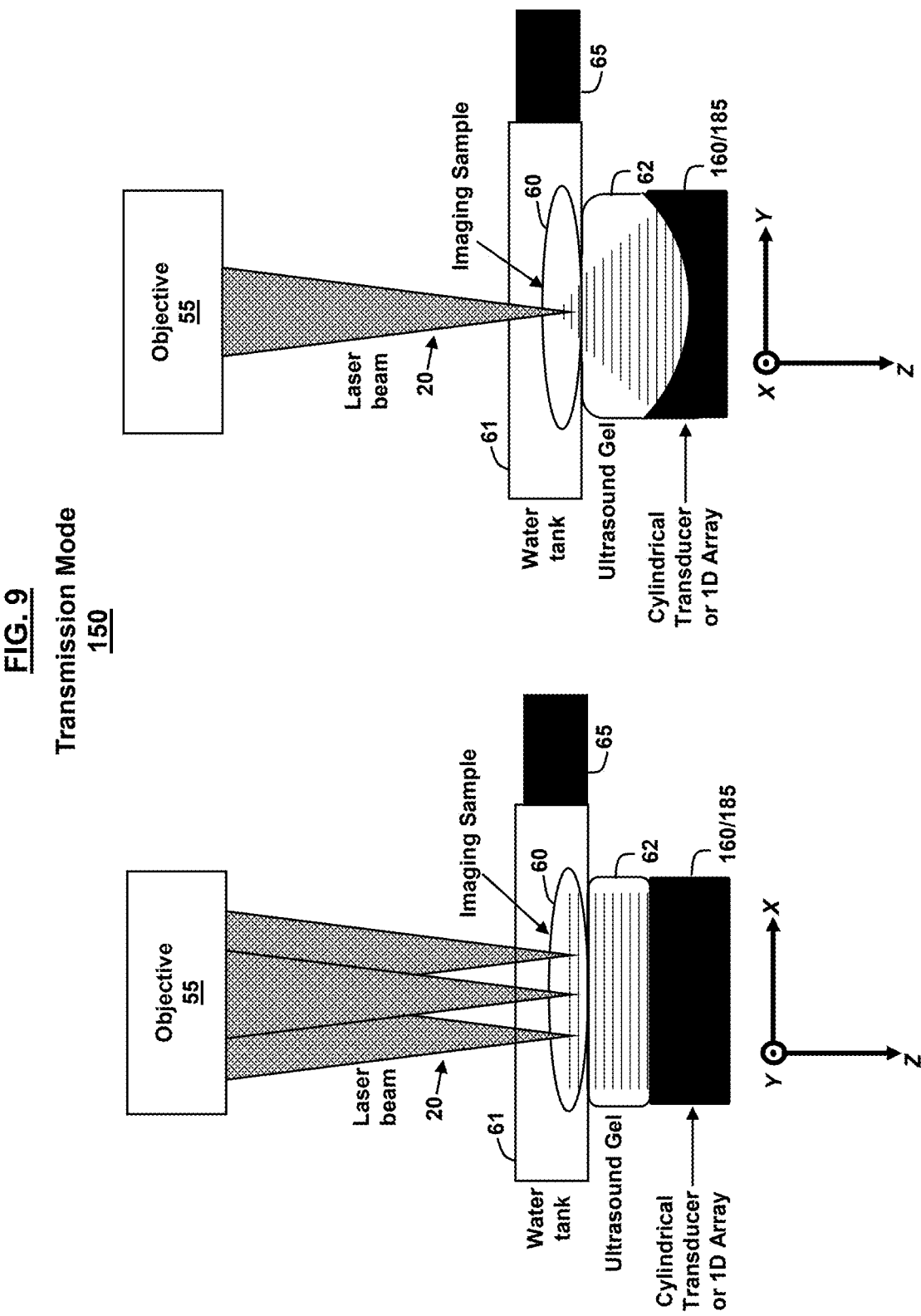
FIG. 9 is a schematic block diagram illustrating the ultrasound detection module in transmission mode configuration, according to an embodiment herein.

FIG. 9, with reference to FIGS. 1 through 8, is a schematic block diagram further illustrating the ultrasound detection module 3 in transmission mode configuration 150. The tissue sample 60 is positioned on a transparent sample holder or thin membrane that provides mechanical support while allowing acoustic transmission. The water tank 61 contains water or other acoustic coupling medium that fills the space surrounding the tissue sample 60 and the ultrasound transducer 85, providing acoustic impedance matching between the tissue and transducer to enable efficient propagation of photoacoustic waves. Ultrasound gel 62 may be applied between the tissue sample 60 and the transparent sample holder to eliminate air gaps that would cause severe acoustic reflection losses at tissue-air interfaces. In the cylindrically focused transducer configuration, the cylindrical transducer 160 is positioned beneath the tissue sample 60 with the one-dimensional line focus 165 maintained at the bottom surface location of the tissue sample 60 through precise positioning, with the transducer mounting including adjustment mechanisms enabling fine control in three dimensions to optimize acoustic coupling and focal alignment. In the linear array configuration, the 1D array 185 is similarly positioned with its elements distributed along a fast scanning axis 35.

Figure 10:
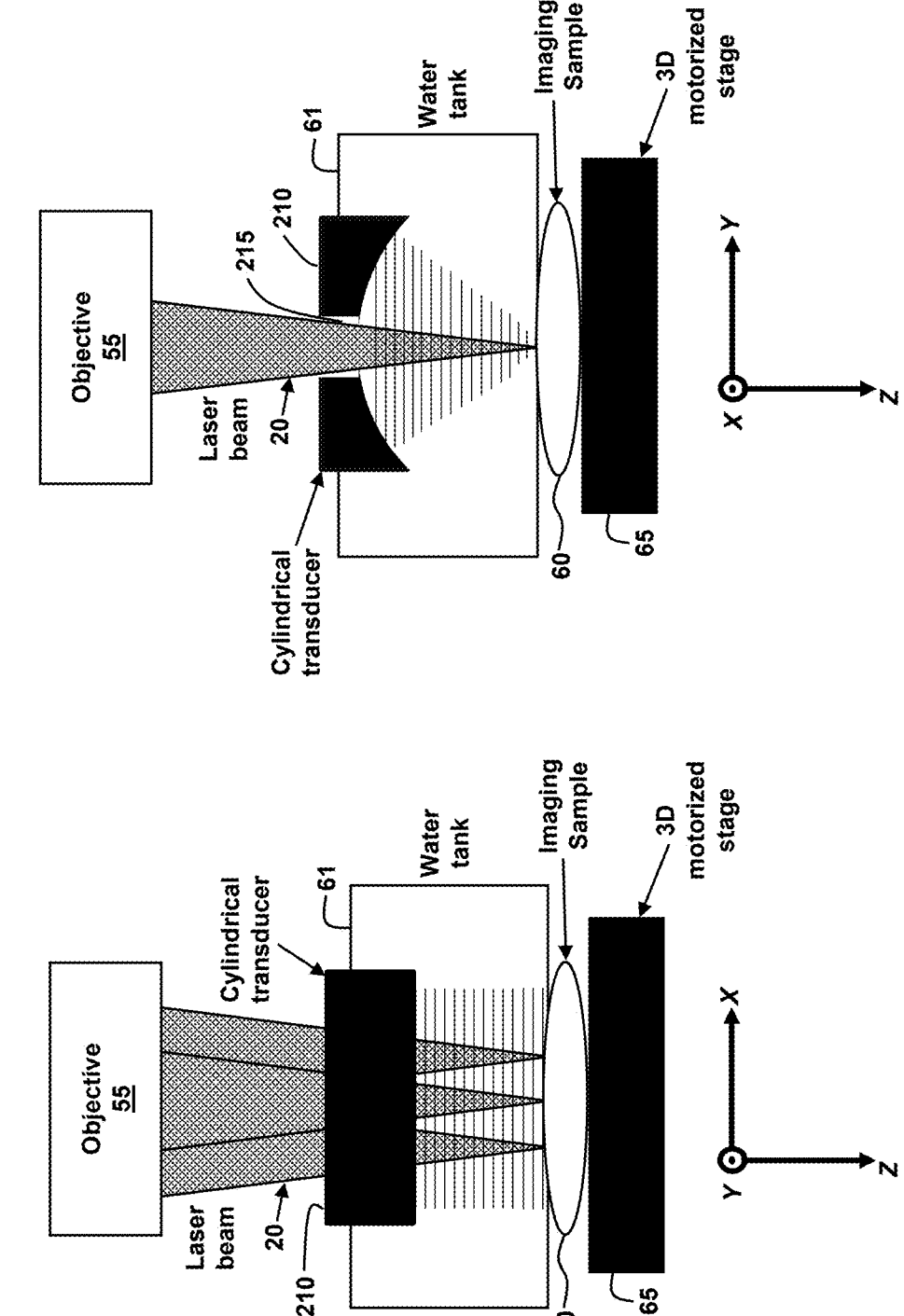
FIG. 10 is a schematic block diagram illustrating the ultrasound detection module in reflection mode with a slit-aperture cylindrical transducer configuration, according to an embodiment herein.

FIG. 10, with reference to FIGS. 1 through 9, is a schematic block diagram illustrating the ultrasound detection module 3 in reflection mode 205a with a slit-aperture cylindrical transducer configuration showing detailed beam and acoustic wave paths. The cylindrically focused transducer element 210 with its central rectangular slit aperture 215 is positioned above the tissue sample 60, for example, at a working distance of five to fifteen millimeters depending on the focal length of the objective lens 55 and the acoustic focal distance of the transducer 210. The water tank 61 and ultrasound gel 62 provide acoustic coupling between the transducer 210 and tissue sample 60. The cylindrically focused transducer element 210 may be embodied as an intact single-piece structure with a slit aperture 215 passing through the central region of the element.

Figure 11:
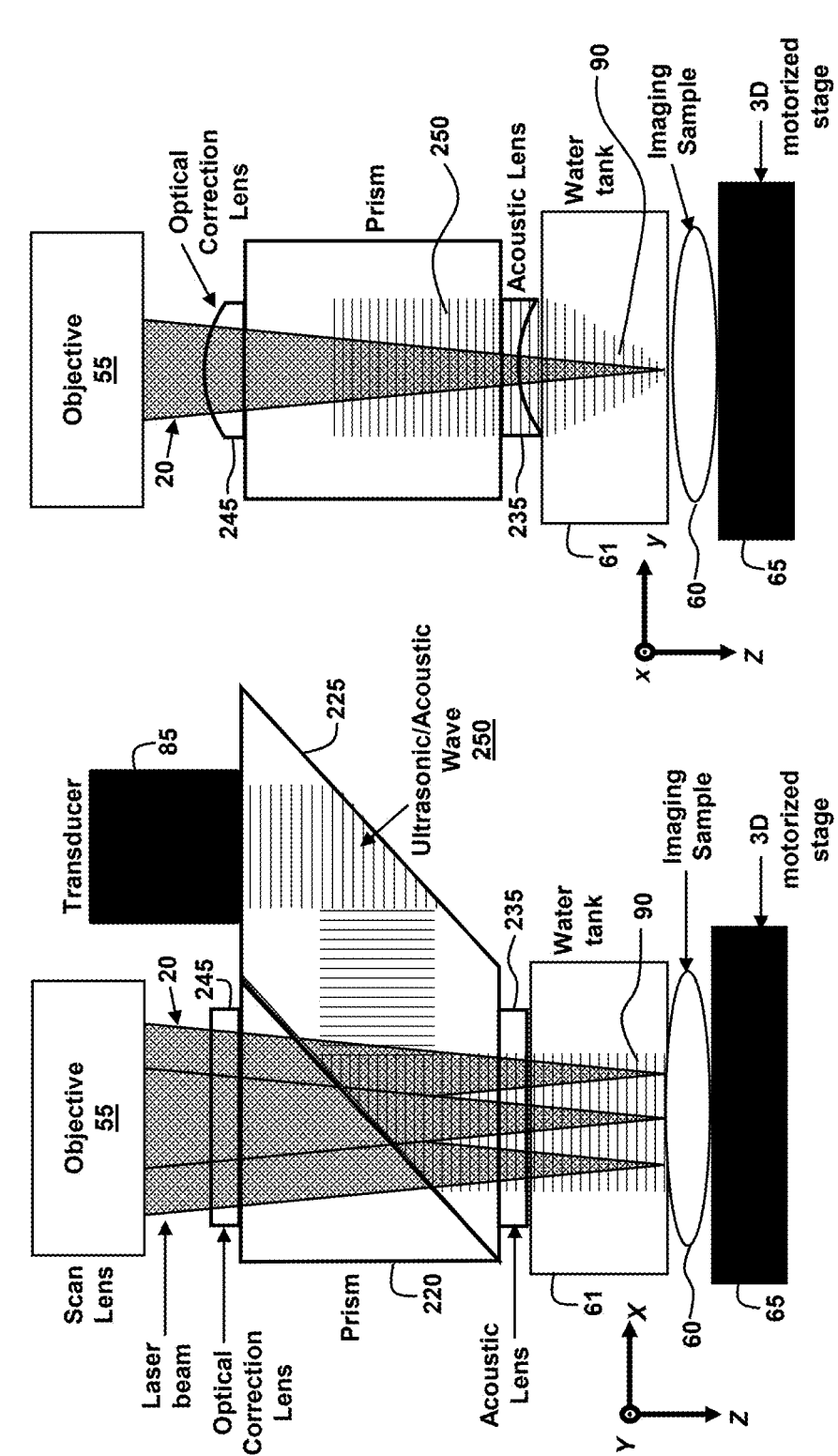
FIG. 11 is a schematic block diagram illustrating the ultrasound detection module in reflection mode with a prism-based transducer configuration, according to an embodiment herein.

FIG. 11, with reference to FIGS. 1 through 10, is a schematic block diagram illustrating the ultrasound detection module 3 in reflection mode 205b with a prism-based transducer configuration showing the complete optical and acoustic beam paths through the prism structure. The water tank 61 immerses the prism assembly and provides acoustic coupling between the rhomboid prism 225 and the tissue sample 60. After focusing by an objective lens 55, the ultraviolet laser beam 20 enters a optical correction lens 245, passes into the right-angle prism 220, traverses the prism body, exits through the angled hypotenuse surface, crosses the silicone oil coupling medium 230, enters the rhomboid prism 225, and exits through the curved bottom surface. Photoacoustic signals 90 generated at the tissue surface propagate upward as acoustic waves 250, enter the rhomboid prism 225 through the acoustic cylindrical lens 235, undergo mode conversion from longitudinal to shear waves at internal interfaces, reflect at a solid-air interface with reconversion back to longitudinal waves, and reach the ultrasound transducer 85 mounted on the top surface of the rhomboid prism 225.

Figure 12:
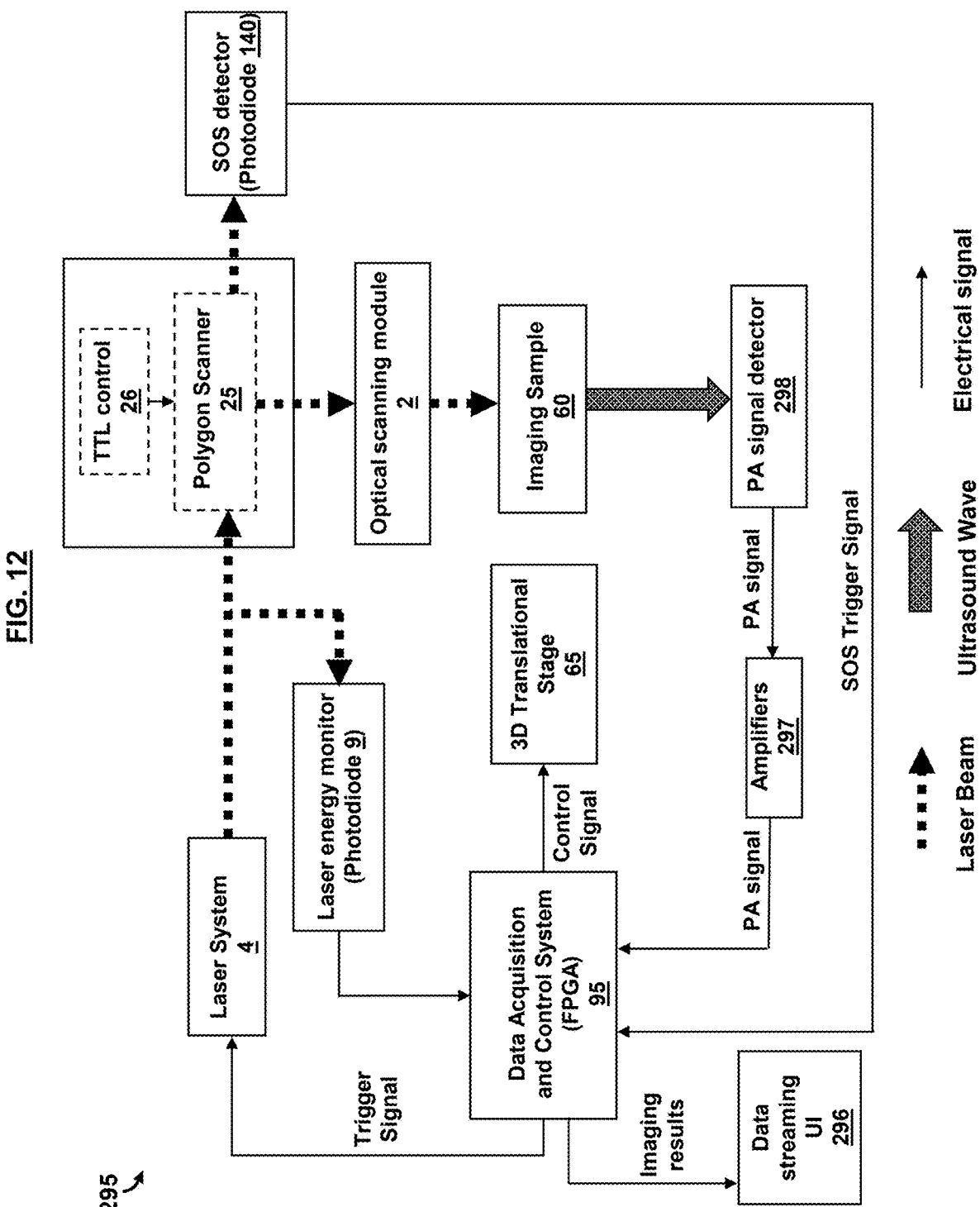
FIG. 12 is a block diagram illustrating system control architecture, according to an embodiment herein.

FIG. 12, with reference to FIGS. 1 through 11, is a block diagram illustrating control system 295 showing the interconnections and data flow between the system components (for ease of understanding and simplicity of the drawing, not all system components are shown in FIG. 12). The data acquisition device 95 serves as the central coordination unit that synchronizes the operation of all subsystems through precisely timed control signals and data transfers. Upon operation, the polygon scanner 25 is driven by TTL control 26, which comprises a function generator or waveform synthesizer (not shown) that outputs constant-frequency TTL pulses maintaining the polygon scanner 25 at its operational rotational speed independently of the main controller timing sequences. Then the data acquisition device 95 sends TTL trigger signals to the laser system 4 commanding the laser to emit optical pulses. In this configuration, the laser firing event must occur before the SOS event, because the SOS photodiode 140 detects the reflected laser pulse to generate the SOS timing signal 145. As the polygon scanner 25 scans and laser emits optical pulses, the data acquisition device 95 receives the SOS trigger signal (e.g., the timing signal 145 (not shown in FIG. 12)) from the photodiode 140 and uses this signal as the start of synchronization reference for each scan line. The controller 100 then generates synchronized TTL signals for the laser system 4, the motorized stages 65 and the data acquisition device 95. The TTL signals for laser system 4 define the precise laser emission frequency and pulse count. The TTL signals for the motorized stage 65 includes position commands specifying the desired X, Y, and Z coordinates, velocity commands defining movement speeds, and acceleration profiles optimizing motion trajectories to minimize settling time while avoiding mechanical vibrations. The TTL signals for data acquisition device 95, defines when analog-to-digital conversion should occur and at what sampling rate, for example, 100 to 500 mega samples per second depending on the transducer frequency characteristics and desired temporal resolution.

The photoacoustic signal detector 298 comprises the ultrasound transducer 85 configured in any of the transmission or reflection mode arrangements 150, 205a, 205b described above such that acoustic waves received by the transducer 85 generate electrical voltage signals through piezoelectric conversion. For both transmission mode 150 and reflection modes 205a and 205b, the electrical signals from the photoacoustic signal detector 298 are transmitted to amplifiers 297 that provide signal preprocessing before digitization. The amplifiers 297 comprise low-noise amplifiers positioned in close proximity to the photoacoustic signal detector 298 to minimize noise pickup in connecting cables, providing voltage gain typically ranging from 40-60 dB to amplify the microvolt-to-millivolt level signals from the transducer up to volt-level signals suitable for the analog-to-digital converter input range of the data acquisition device 95. The amplifiers 297 may include variable gain stages allowing adjustment of amplification factors to accommodate different tissue types and imaging depths, bandpass filtering to remove out-of-band noise while preserving the frequency content of photoacoustic signals. The amplified signals from the amplifiers 297 are fed to the data acquisition device 95 which comprises a high-speed data acquisition device operating at a high sampling rate such as 500 megahertz, digitizing the analog voltage waveforms at the sampling rate commanded by the controller 100, where the 500 megahertz sampling rate provides temporal resolution of two nanoseconds between successive samples enabling accurate capture of the high-frequency acoustic waveforms without aliasing. The data acquisition device 95 may be implemented as part of a reconfigurable input/output device equipped with a field-programmable gate array that provides the hardware flexibility to coordinate multiple high-speed operations simultaneously. The controller 100, which may comprise or interface with the reconfigurable input/output device equipped with the field-programmable gate array, is configured to coordinate the firing of the pulsed laser source 15, the motor control of the motorized stage 65, and the data acquisition by the data acquisition device 95, ensuring precise temporal synchronization between optical excitation, mechanical positioning, and signal acquisition. The controller 100 receives digitized photoacoustic waveform data from the data acquisition device 95. The controller 100 also receives pulse energy measurements from the photodiode 9 that monitors the laser output through the beam sampler 8, using these measurements for real-time normalization of photoacoustic signal amplitudes to compensate for pulse-to-pulse laser energy variations.

The data acquisition device 95 comprises computational hardware including the controller 100, memory subsystems, storage devices, and communication interfaces that collectively manage system operation and data processing. The memory subsystems include high-speed random access memory (RAM) for temporary storage of acquired waveform data, intermediate processing results, and control variables. The controller 100 executes control software that implements the synchronization algorithms, motion control logic, image reconstruction procedures, and user interface functions.

The data acquisition device 95 includes a data streaming user interface (UI) 296 that provides real-time visualization of imaging results as data is acquired, enabling immediate feedback during the scanning process. The data streaming UI 296 comprises software executing on the controller 100 or on a separate display computer communicatively coupled to the controller 100, implemented using graphical user interface frameworks such as Lab VIEW or custom applications built with visualization libraries. The data streaming UI 296 receives image data from the controller 100 as each scan line is completed, performs rapid image reconstruction by extracting amplitude values from the digitized waveforms, arranges these values into the appropriate pixel positions in a two-dimensional display buffer, and updates the display device to show the growing image as scanning progresses. This real-time streaming capability allows operators to monitor image quality during acquisition and make immediate adjustments to system parameters if needed, such as modifying laser power, adjusting focus position, or repositioning the sample. The data streaming UI 296 may display multiple visualization modes simultaneously, including the raw photoacoustic amplitude map, energy-normalized images after applying corrections for laser pulse variations, depth-encoded color overlays showing surface topology from the contour map 110, and status indicators reporting scanning progress, estimated time remaining, and system health metrics.

Figure 13A:
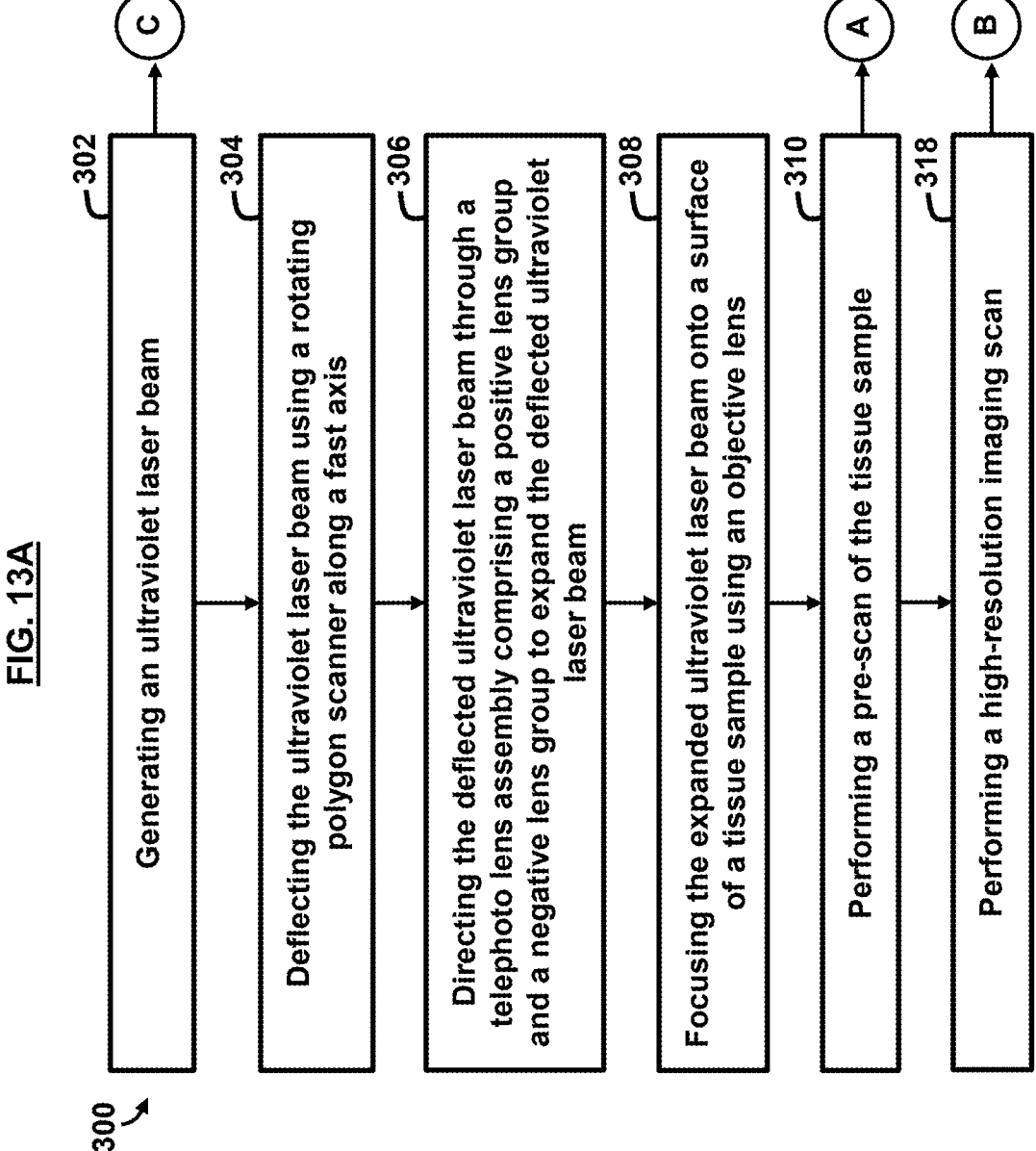
FIG. 13A is a flow diagram illustrating a method for rapid intraoperative pathology imaging showing the main process steps, according to an embodiment herein.

FIGS. 13A through 13H, with reference to FIGS. 1 through 12, are flowcharts illustrating a method 300 for rapid intraoperative pathology imaging. As shown in FIG. 13A, the method 300 comprises generating (302) an ultraviolet laser beam 20 having a wavelength specifically selected to coincide with absorption maxima of nucleic acids and proteins in biological tissue, preferably at 266 nanometers, such that this wavelength enables visualization of cellular nuclei and cytoplasmic structures without chemical staining by exploiting the strong optical absorption of DNA, RNA, and aromatic amino acids at ultraviolet wavelengths. The method 300 comprises deflecting (304) the ultraviolet laser beam 20 using a rotating polygon scanner 25 along a fast axis 35, such that the polygon scanner 25 rotates continuously at constant angular velocity, for example, at 10,000 to 45,000 revolutions per minute, and each of the plurality of reflective facets 30 sequentially intercepts and deflects the ultraviolet laser beam 20 through a predetermined angular range to achieve high-speed line scanning at rates exceeding several thousand lines per second. The method 300 comprises directing (306) the deflected ultraviolet laser beam 20 through a telephoto lens assembly 40 comprising a positive lens group 45 and a negative lens group 50 to expand the deflected ultraviolet laser beam 20, such that the telephoto configuration expands the beam diameter to fill the entrance aperture of the objective lens 55 while simultaneously compressing the angular divergence of the scanned beam to maintain telecentric imaging conditions and minimize field curvature aberrations across the scanning field.

The method 300 comprises focusing (308) the expanded ultraviolet laser beam 20 onto a surface of a tissue sample 60 using an objective lens 55. The objective lens 55 may comprise an F-theta scan lens configured such that image height is proportional to scan angle rather than the tangent of scan angle, thereby ensuring uniform scanning velocity at the sample plane and maintaining constant spot size across the entire scan range. The method comprises performing (310) a pre-scan of the tissue sample 60 and performing (318) a high-resolution imaging scan. These steps (310), (318) are further described below with reference to FIGS. 13B and 13C, respectively.

Figure 13B:
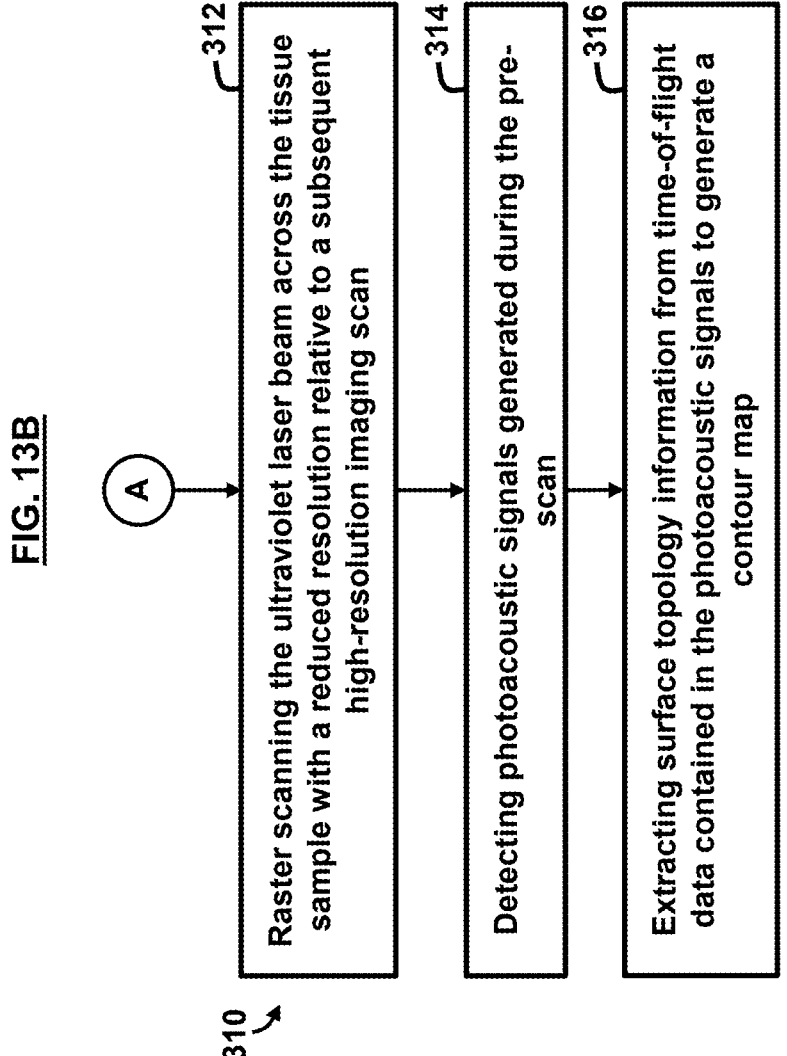
FIG. 13B is a flow diagram illustrating the pre-scan process including raster scanning, signal detection, and contour map generation, according to an embodiment herein.

The method 300 comprises performing (310) a pre-scan of the tissue sample 60 as further shown in FIG. 13B. The pre-scan is executed with reduced spatial resolution relative to subsequent high-resolution imaging to enable rapid acquisition of surface topology information across the imaging area. Performing (310) the pre-scan comprises raster scanning (312) the ultraviolet laser beam 20 across the tissue sample 60 with a reduced resolution relative to a subsequent high-resolution imaging scan, such that the reduced resolution is achieved by selecting spatial sampling intervals that are 10-100 times larger than the high-resolution pixel spacing. Performing (310) the pre-scan comprises detecting (314) photoacoustic signals 90 generated during the pre-scan, such that each laser pulse absorbed by the tissue sample 60 generates localized thermoelastic expansion that generates acoustic waves 250 propagating toward the ultrasound transducer 85, which converts the acoustic waves 250 into electrical voltage waveforms through piezoelectric transduction, and these waveforms are digitized by the data acquisition device 95 to create digital representations of the photoacoustic signals 90. Performing (310) the pre-scan comprises extracting (316) surface topology information from time-of-flight data contained in the photoacoustic signals 90 to generate a contour map 110, such that the extraction process involves analyzing each digitized waveform to identify temporal positions of characteristic features corresponding to the tissue surface including maximum positive and negative peaks, calculating the center position between these peaks which corresponds to the time-of-flight from tissue surface to transducer 85, converting the time-of-flight to depth values by multiplying by the acoustic velocity in the coupling medium and applying geometric corrections, compiling all depth measurements into a two-dimensional raw topology array, applying interpolation algorithms such as bilinear or bicubic interpolation to generate depth values at all high-resolution pixel positions, and optionally applying spatial filtering such as Gaussian smoothing to remove noise and ensure smooth Z-axis motion trajectories during subsequent high-resolution scanning.

Figure 13C:
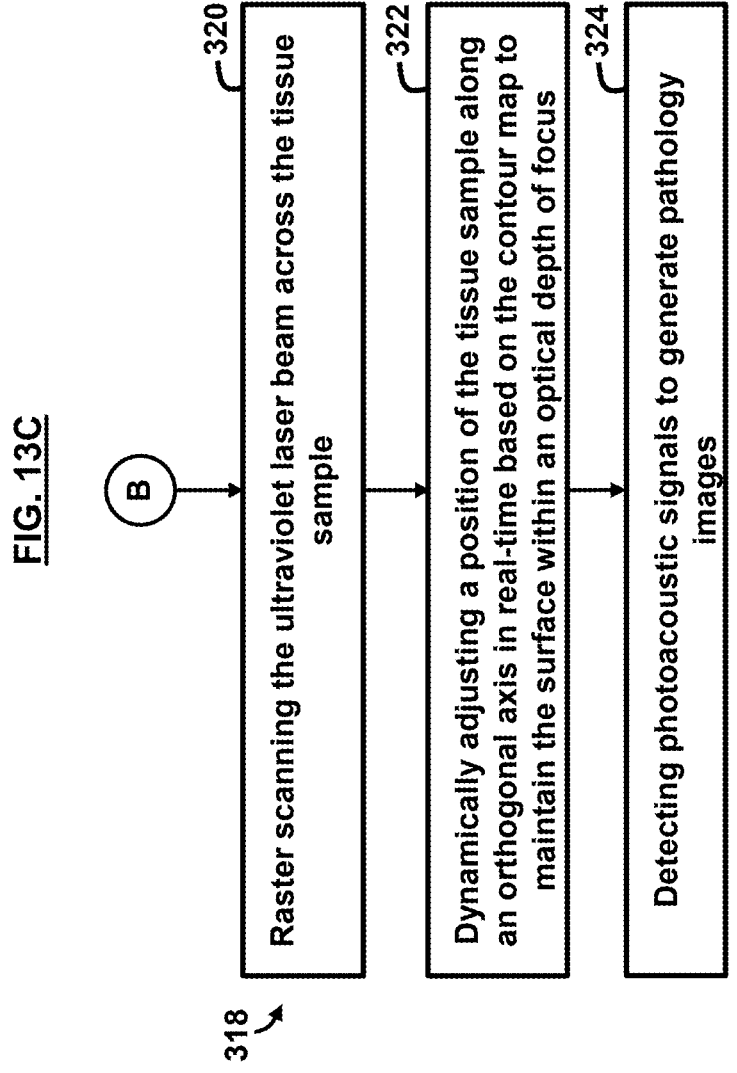
FIG. 13C is a flow diagram illustrating the high-resolution imaging scan process including dynamic position adjustment and pathology image generation, according to an embodiment herein.

The method 300 comprises performing (318) a high-resolution imaging scan as further shown in FIG. 13C, such that the high-resolution scan acquires detailed pathology images with spatial resolution sufficient for subcellular visualization and accurate diagnostic interpretation. Performing (318) the high-resolution imaging scan comprises raster scanning (320) the ultraviolet laser beam 20 across the tissue sample 60, such that the polygon scanner 25 deflects the beam 20 along the fast axis 35 while the motorized stage 65 incrementally translates the tissue sample 60 along the slow axis with step sizes equal to or smaller than the optical resolution to achieve isotropic pixel dimensions, and the controller 100 triggers the pulsed laser source 15 to emit pulses at precise time intervals determined by the desired pixel spacing and the scanning velocity at the sample plane. Performing (318) the high-resolution imaging scan comprises dynamically adjusting (322) a position of the tissue sample 60 along an orthogonal axis 80 in real-time based on the contour map 110 to maintain the surface within optical depth of focus, such that for each pixel position the controller 100 retrieves the corresponding depth value from the stored contour map 110 and commands the motorized stage 65 to translate vertically to that Z-position, thereby compensating for surface height variations that would otherwise cause defocusing and resolution degradation. Performing (318) the high-resolution imaging scan comprises detecting (324) photoacoustic signals 90 to generate pathology images, such that the ultrasound transducer 85 detects acoustic waves generated by each laser pulse, the data acquisition device 95 digitizes the signals at sampling rates of 100-500 megasamples per second, for example, amplitude values are extracted from each waveform by detecting maximum absolute amplitude or integrating over a temporal window, the extracted amplitudes are normalized by dividing by corresponding laser pulse energy measurements from photodiode 9 to compensate for pulse-to-pulse variations, and the normalized amplitude values are arranged into a two-dimensional array according to their X-Y spatial coordinates to form the final photoacoustic microscopy image revealing cellular and subcellular morphology suitable for pathological assessment.

FIG. 13D illustrates that generating (302) the ultraviolet laser beam 20 may comprise emitting (330) a pulsed laser beam 125 at a first wavelength such as 532 nanometers, such that the pulsed laser source 15 comprises a high-repetition-rate frequency-doubled solid-state laser operating at megahertz repetition rates with pulse durations in the nanosecond regime, for example, 1-10 nanoseconds, which is sufficiently short to satisfy the stress confinement condition required for efficient photoacoustic signal generation such that the pulse duration is shorter than the time for stress waves to propagate across the heated volume. Generating (302) the ultraviolet laser beam 20 may comprise converting (332) the first wavelength to an ultraviolet wavelength such as 266 nanometers through second harmonic generation 126 using a nonlinear crystal 115 and a dispersive prism 127, such that the 532 nanometer laser beam 125 is focused through the nonlinear crystal 115 then through the dispersive prism 127 such that the purified 266 nanometer ultraviolet beam 20 continues along the primary optical path toward the beam expansion and spatial filtering components.

FIG. 13E illustrates that the method 300 may further comprise detecting (334) a start-of-scan (SOS) signal 145 using an optical fiber 130 positioned at a beginning of a scanning trajectory, such that the optical fiber 130 has a stripped tip 135 positioned such that when each facet 30 of the rotating polygon scanner 25 begins its active scanning period the deflected ultraviolet laser beam 20 strikes the cylindrical side surface of the stripped tip 135, a portion of the incident light couples into the optical fiber 130 through side illumination and propagates to a photodiode 140 positioned at the opposite end of the fiber, the photodiode 140 converts the optical pulse to an electrical pulse through absorption of ultraviolet photons and generation of electron-hole pairs creating photocurrent, and this electrical pulse is amplified to form the start-of-scan timing signal 145 with amplitude suitable for digital logic processing. The method 300 may further comprise synchronizing (336) laser pulsing, data acquisition, and stage movement based on the start-of-scan signal 145, such that the controller 100 receives the start-of-scan timing signal 145 and uses it as a temporal reference point defining the beginning of each scan line, calculates expected beam positions as a function of time after the start-of-scan signal based on polygon scanner geometry and rotational velocity, generates laser trigger pulses at calculated times such that laser pulses occur when the beam is at desired pixel positions along the scan line with time intervals between successive triggers equal to pixel spacing divided by scanning velocity, generates data acquisition trigger pulses synchronized with the laser triggers to initiate analog-to-digital conversion at appropriate times to capture photoacoustic signals, and commands motorized stage motion to increment position along the slow axis during or after each complete scan line, thereby ensuring accurate spatial registration of all acquired data and preventing geometric distortions in reconstructed images.

Detecting (324) photoacoustic signals 90 may comprise detecting the photoacoustic signals 90 in transmission mode 150 using a cylindrically focused ultrasound transducer 160 positioned opposite to an illumination side of the tissue sample 60, such that the cylindrically focused transducer 160 provides a one-dimensional line focus 165 where acoustic sensitivity is maximized, the ultraviolet laser beam 20 is maintained confocal with this acoustic line focus 165 and scans along the line focus as the polygon scanner 25 rotates, photoacoustic waves generated at the illuminated tissue surface propagate downward through the tissue thickness, the coupling medium, and are received by the transducer element. The confocal line-scanning geometry provides superior signal-to-noise ratio by maximizing acoustic sensitivity along the focal line where laser scanning occurs while naturally suppressing acoustic noise from out-of-focus regions.

Detecting (324) photoacoustic signals 90 may further comprise detecting the photoacoustic signals 90 in reflection mode 205a through a cylindrically focused ultrasound transducer 85 with a slit aperture 215, such that the ultraviolet laser beam 20 passes coaxially through the slit aperture 215, the slit aperture 215 comprises a narrow rectangular opening cut through the piezoelectric material along the length of the cylinder axis such that the coaxial arrangement enables the laser beam to travel downward through the slit aperture 215 to reach the tissue sample 60 while acoustic waves generated at the tissue surface propagate upward to the active transducer areas of the ultrasound transducer 85.

FIG. 13F illustrates that the method 300 may further comprise applying (338) a conditional diffusion model 265 to the pathology images to generate virtual histologically-stained images 280 that simulate conventional histological staining without physical staining of the tissue sample 60, such that the conditional diffusion model 265 comprises a neural network 270 implementing a generative modeling approach that learns to reverse a gradual noising process, the model receives photoacoustic microscopy images 275 as input conditioning and generates synthetic histologically-stained appearances that replicate the color, contrast, and morphological features of hematoxylin and eosin stained tissue.

FIG. 13G illustrates that the method 300 may further comprise applying (340) a semantic segmentation network 285 to the virtual histologically-stained images 280 to automatically detect tumor margins within the tissue sample 60, such that the semantic segmentation network 285 implements pixel-wise classification assigning each pixel a class label indicating whether it belongs to tumor region 290*a* or non-tumor region 290*b*. The network 285 receives as input the virtual histologically-stained images 280 and may also receive the original photoacoustic microscopy images 275 as additional input channels to leverage complementary absorption-based contrast. The network 285 automatically delineates tumor regions 290*a* and non-tumor regions 290*b* to provide decision support for surgeons during intraoperative procedures, enabling rapid assessment of whether surgical margins are clear of tumor or whether additional tissue removal is necessary.

FIG. 13H illustrates that the method 300 may further comprise training (342) a conditional diffusion model 265 for virtual staining using training data comprising photoacoustic microscopy images 275 acquired with ultraviolet laser excitation and corresponding histologically-stained images 280, such that the training data comprises paired examples obtained from same tissue specimens with careful spatial registration to establish pixel-level correspondence, the training process involves observing how the diffusion model learns to map from the photoacoustic domain with its DNA/RNA absorption contrast at 266 nanometers to the histological domain with its synthetic hematoxylin and eosin appearance. The conditional diffusion model 265 is trained using a loss function comprising at least one of reconstruction loss calculated as L1 or L2 distance between generated and ground truth images to ensure basic fidelity, perceptual loss based on features extracted from a pretrained convolutional neural network such as VGG to encourage similar high-level perceptual characteristics, adversarial loss when integrated with a discriminator network to improve realism especially for unpaired or weakly paired inputs, structural preservation loss such as structural similarity index measure to enforce consistency in nuclear boundaries and cellular morphology, or segmentation consistency loss that compares outputs of a pretrained nuclei or tissue segmentation network applied to both generated virtual H&E and source UV-PAM images to enforce alignment in cellular morphology across modalities. The method 300 may further comprise training (344) a semantic segmentation network 285 for tumor margin detection using annotated datasets comprising labeled tumor regions 290*a* and non-tumor regions 290*b*, such that the annotated datasets comprise histological images with pixel-level tumor annotations created by expert pathologists, the training employs specialized loss functions including Dice loss calculated as one minus twice the intersection of predicted and true positive pixels divided by the sum of predicted positive and true positive pixels to directly optimize overlap while handling class imbalance, cross-entropy loss combined with Dice loss to provide additional gradient signal especially during early training, and boundary-aware regularization terms that apply higher weight to pixels near tumor boundaries to penalize errors in these regions more heavily than errors in tissue interiors, thereby encouraging accurate delineation of tumor margins which is particularly important for surgical applications where precise margin assessment directly impacts clinical outcomes.

Figure 14A:
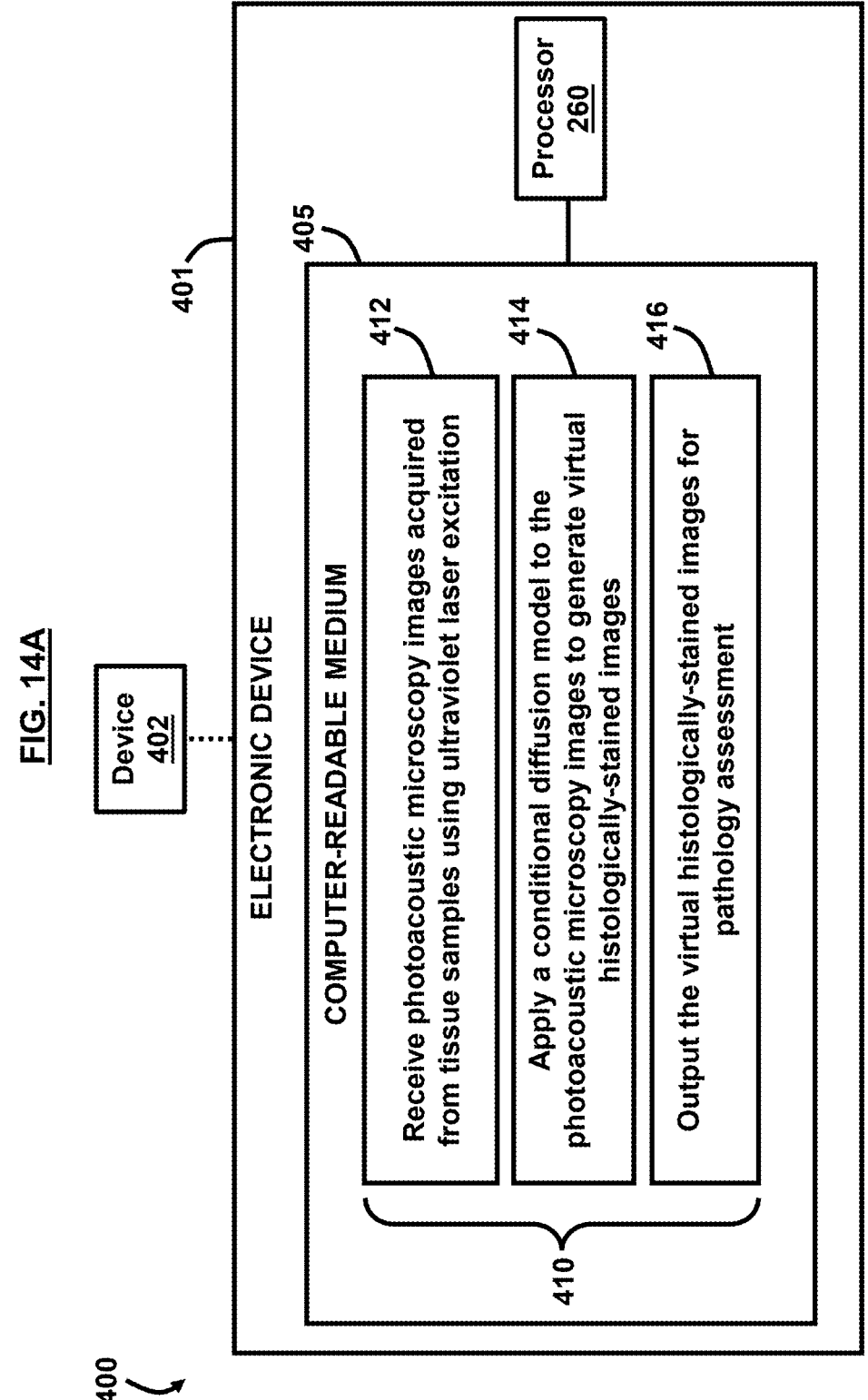
FIG. 14A is a block diagram illustrating a non-transitory computer-readable medium and processor architecture for executing virtual staining operations, according to an embodiment herein.

FIGS. 14A and 14B, with reference to FIGS. 1 through 13H, illustrates another example of a system 400 for performing rapid intraoperative pathology imaging. In FIGS. 14A and 14B, the various blocks are not necessarily sequential and may be practiced independently from each other and/or in any suitable order. According to an example, the system 400 comprises an electronic device 401 containing a computer-readable storage medium 405, and a remote communication device 402 communicatively linked to the electronic device 401. In the example of FIGS. 14A and 14B, the electronic device 401 includes the processor 260 and the computer-readable storage medium 405. Processor 260 may include a central processing unit, microprocessors, hardware engines, and/or other hardware devices suitable for retrieval and execution of instructions stored in a computer-readable storage medium 405, for example. Processor 260 may fetch, decode, and execute computer-executable instructions 410 to enable execution of locally-hosted or remotely-hosted applications for controlling action of the electronic device 401. The remotely-hosted applications may be accessible on remotely-located devices; for example, the remote communication device 402. For example, the remote communication device 402 may be a laptop computer, tablet device, smartphone, or notebook computer. As an alternative or in addition to retrieving and executing instructions, processor 260 may include electronic circuits including a number of electronic components for performing the functionality of the computer-executable instructions 410.

The computer-readable storage medium 405 may be any electronic, magnetic, optical, or other physical storage device that stores executable instructions. Thus, the computer-readable storage medium 405 may be, for example, Random Access Memory, an Electrically-Erasable Programmable Read-Only Memory, volatile memory, non-volatile memory, flash memory, a storage drive (e.g., a hard drive), a solid-state drive, optical drive, any type of storage disc (e.g., a compact disc, a DVD, etc.), and the like, or a combination thereof. In one example, the computer-readable storage medium 405 may include a non-transitory computer-readable storage medium 405. The computer-readable storage medium 405 may be encoded with executable instructions for enabling execution of remotely-hosted applications accessed on the remote communication device 302. In an example, the processor 260 of the electronic device 401 executes the computer-executable instructions 410 that when executed cause the electronic device 401 to perform computer-executable instructions 410.

As shown in the example of FIG. 14A, the non-transitory computer-readable medium 405 is configured for storing instructions 410 that, when executed by a processor 260, cause the processor 260 to receive (412) photoacoustic microscopy images 275 acquired from tissue samples 60 using ultraviolet laser excitation. The receiving operation (412) comprises reading image data from memory locations where the photoacoustic microscopy images 275 have been stored following acquisition by the photoacoustic microscopy system 10, such that the image data may be stored in various formats including raw pixel arrays with integer or floating-point values representing signal amplitudes, compressed image formats such as JPEG or PNG, or specialized medical imaging formats such as DICOM that include metadata describing acquisition parameters and patient information. The receiving operation (412) may include validation steps to verify data integrity such as checking image dimensions match expected values, confirming that pixel values fall within physically reasonable ranges, and verifying that required metadata fields are present. The receiving operation (412) may involve loading image data from non-volatile storage into high-speed random access memory to enable rapid processing.

When executed by the processor 260, the instructions 410 cause the processor 260 to apply (414) a conditional diffusion model 265 to the photoacoustic microscopy images 275 to generate virtual histologically-stained images 280. The conditional diffusion model 265 comprises a denoising neural network 270 trained to reverse a forward diffusion process while being conditioned on the photoacoustic microscopy images 275. The denoising neural network 270 learns to reverse corruption by iteratively removing noise, starting from a noisy input and progressively refining it toward a clean output. The conditioning on the photoacoustic microscopy images 275 ensures that the generated virtual stains maintain correspondence with the structural features present in the input photoacoustic data rather than generating arbitrary histological appearances. During inference, the applying operation (414) involves executing multiple forward passes through the denoising neural network 270 such that each step receives the partially denoised image from the previous step along with the conditioning photoacoustic image 275 and outputs a refined estimate with reduced noise.

When executed by the processor 260, the instructions 410 cause the processor 260 to output (416) the virtual histologically-stained images 280 for pathology assessment. The outputting operation (416) comprises writing the generated virtual histologically-stained images 280 to designated memory locations or storage devices where they can be accessed by display systems, image analysis algorithms, or electronic medical record systems. The outputting operation (416) may generate multiple output formats simultaneously, including high-resolution images for detailed examination by pathologists and compressed formats for network transmission or long-term archival. The virtual histologically-stained images 280 produced by the outputting operation (416) replicate the appearance of conventional hematoxylin and eosin stained sections with purple-blue nuclei and pink cytoplasmic regions, enabling pathologists to apply their existing diagnostic expertise without requiring retraining to interpret novel contrast mechanisms.

FIG. 14B, with reference to FIGS. 1 through 14A, is a block diagram illustrating a non-transitory computer-readable medium 405 and processor architecture for executing virtual staining with preprocessing and segmentation operations. The instructions 410 may cause the processor 260 to preprocess (418) the photoacoustic microscopy images 275 prior to applying (414) the conditional diffusion model 265. The preprocessing operation (418) improves the quality and consistency of input data to the neural network, thereby enhancing the accuracy and reliability of the generated virtual stains. The preprocessing may include performing at least one of background flattening, global intensity normalization, filter-based denoising, or multi-channel enhancement. Background flattening comprises correcting for spatially-varying baseline signal levels that arise from uneven illumination, acoustic coupling variations, or detector sensitivity variations across the field of view. Background flattening may be implemented by estimating a smooth background surface through polynomial fitting or morphological operations such as rolling ball background subtraction, then subtracting this background from the original image to produce a flattened image with uniform baseline. Global intensity normalization comprises scaling pixel intensity values to a standardized range to compensate for variations in laser beam energies between different specimens or imaging sessions. The normalization may involve linear scaling to map the minimum and maximum observed intensities to predetermined output values such as zero and one, or statistical normalization to achieve specified mean and standard deviation values across the image.

The preprocessing operation (418) may include filter-based denoising to reduce random fluctuations in pixel values caused by electronic noise in the data acquisition system or acoustic speckle effects. Filter-based denoising may employ Gaussian filtering which convolves the image with a Gaussian kernel to smooth local intensity variations, median filtering which replaces each pixel with the median value in its neighborhood to suppress impulse noise while preserving edges, bilateral filtering which applies edge-preserving smoothing by weighting neighboring pixels based on both spatial proximity and intensity similarity, or non-local means filtering which exploits self-similarity by averaging pixels that have similar surrounding neighborhoods even if spatially distant. The preprocessing operation (418) may include multi-channel enhancement such that additional derived channels are computed from the original photoacoustic image and concatenated to create a multi-channel input for the neural network.

The instructions 410 may cause the processor 260 to apply (420) a semantic segmentation network 285 to the virtual histologically-stained images 280 to generate a segmentation map identifying tumor regions 290a and non-tumor regions 290b. The applying operation (420) comprises executing forward pass inference through the semantic segmentation network 285, which typically has an encoder-decoder architecture similar to the diffusion model but optimized for pixel-wise classification rather than image generation. The encoder pathway progressively down-samples the input image while extracting increasingly abstract features through sequences of convolutional layers, normalization layers, and nonlinear activation functions such as rectified linear units. The decoder pathway upsamples the encoded features back to the original image resolution while incorporating fine-grained spatial information through skip connections from the encoder. The final layer of the segmentation network produces a probability map with the same spatial dimensions as the input image.

The semantic segmentation network 285 may receive as input both the virtual histologically-stained images 280 and the photoacoustic microscopy images 275, implementing a multi-modal fusion approach that leverages complementary information from both imaging modalities. The semantic segmentation network 285 may be trained using a loss function comprising at least one of Dice loss, cross-entropy loss, or boundary-aware regularization terms. Dice loss directly measures the overlap between predicted segmentation and ground truth annotation, calculated as one minus twice the intersection area divided by the sum of predicted and true positive areas, providing a differentiable metric that can be optimized through gradient descent while inherently balancing the importance of tumor and non-tumor regions even when they occupy substantially different proportions of the image.

The embodiments herein may also include tangible and/or non-transitory computer-readable storage media for carrying or having computer-executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose computer or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network. If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 15:
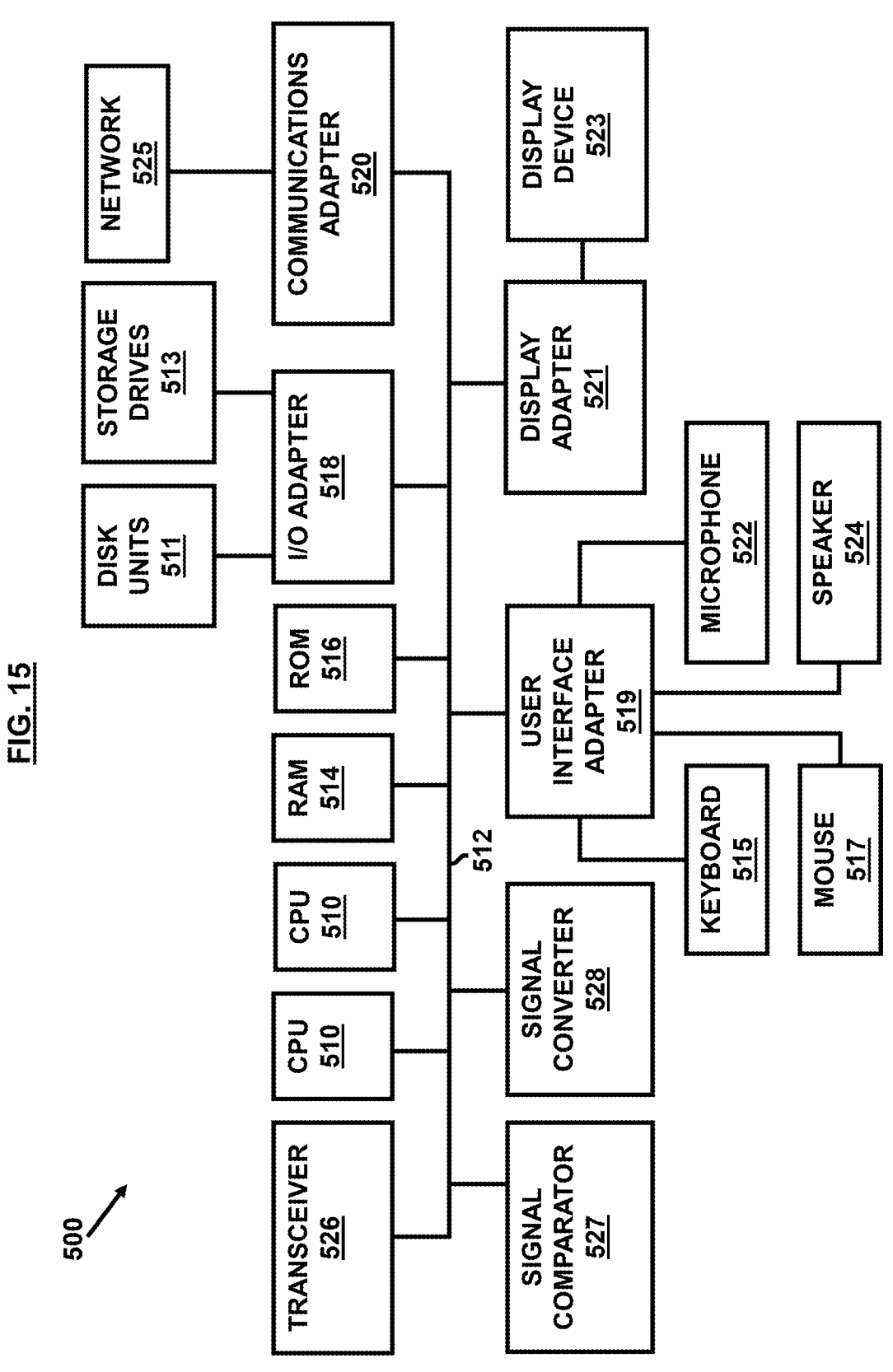
FIG. 15 is a block diagram illustrating computer architecture used in accordance with the embodiments herein.

A representative hardware environment for practicing the embodiments herein is depicted in FIG. 15, with reference to FIGS. 1 through 14, according to an example. This schematic example drawing illustrates a hardware configuration of an information handling/computer system 500 in accordance with the embodiments herein. For example, the system 500 comprises at least one processor or central processing unit (CPU) 510. The CPUs 510 may be interconnected via system bus 512 to various devices such as a random access memory (RAM) 514, read-only memory (ROM) 516, and an input/output (I/O) adapter 518. The I/O adapter 518 can connect to peripheral devices, such as disk units 511 and tape drives 513, or other program storage devices that are readable by the system 500. The system 500 can read the inventive instructions on the program storage devices and follow these instructions to execute the methodology of the embodiments herein. The system 500 may further include a user interface adapter 519 that connects a keyboard 515, mouse 517, speaker 524, microphone 522, and/or other user interface devices such as a touch screen device (not shown) to the bus 512 to gather user input. Additionally, a communication adapter 520 may connect the bus 512 to a data processing network 525, and a display adapter 521 may connect the bus 512 to a display device 523, which may be embodied as an output device such as a monitor, printer, or transmitter, for example. Further, a transceiver 526, a signal comparator 527, and a signal converter 528 may be connected with the bus 512 for processing, transmission, receipt, comparison, and conversion of electric or electronic signals.

FIG. 16, with reference to FIGS. 1 through 15, is a data pipeline diagram illustrating the complete workflow 600 from pre-scan through high-resolution imaging, image preprocessing, virtual staining using a diffusion model, and margin detection. The workflow begins with a rapid pre-scan phase 602 that acquires surface topology data from the tissue sample 60, which is processed to generate the contour map 110 for subsequent focus compensation. The pipeline then proceeds to the actual scan phase 604 where high-resolution imaging occurs and photoacoustic signals 90 are acquired while dynamically adjusting sample position based on the contour map, producing raw photoacoustic microscopy images 275 that reveal optical absorption distributions at ultraviolet wavelengths.

Next, the acquired photoacoustic images 275 undergo a preprocessing phase 606 to enhance quality and consistency, then are input to the conditional diffusion model 265 in phase 608 which generates virtual histologically-stained images 280 replicating conventional H&E appearance. The semantic segmentation network 285 analyzes these virtual stains to automatically identify tumor regions 290a and non-tumor regions 290b, producing segmentation maps that delineate tumor margins in phase 610. The complete pipeline from tissue mounting through final margin detection executes within minutes, with results displayed in real-time through the data streaming user interface 296, enabling intraoperative surgical decision-making. The data pipeline workflow 600 illustrates how hardware subsystems including the laser excitation module 1, high-speed scanning module 2, ultrasound detection module 3, and control system 295 work in concert with software components including the image reconstruction algorithms, preprocessing operations, conditional diffusion model 265, and semantic segmentation network 285 to provide comprehensive pathology assessment without chemical staining or tissue destruction.

The embodiments described herein provide a photoacoustic microscopy system 10, 295, 400 and method 300 that overcome the fundamental limitations of conventional intraoperative pathology techniques by integrating high-repetition-rate ultraviolet laser excitation from pulsed laser source 15, high-speed polygon scanner 25 beam deflection, telephoto lens assembly 40 beam conditioning, objective lens 55 focusing, and intelligent surface contour compensation through motorized stage 65 control based on contour map 110 generated during pre-scan operations. The ultrasound transducer 85 detects photoacoustic signals 90 in various transmission and reflection mode configurations, while the controller 100 coordinates all subsystems to enable rapid acquisition of diagnostic-quality images from fresh surgical specimens. The embodiments herein may further incorporate artificial intelligence components including conditional diffusion model 265 for generating virtual histologically-stained images 280 and semantic segmentation network 285 for automated tumor margin detection, providing surgeons with real-time pathological assessment capabilities that enable informed intraoperative decision-making without the delays, artifacts, and tissue destruction associated with frozen section analysis.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A photoacoustic microscopy system for intraoperative pathology imaging, the system comprising:
a pulsed laser source that generates an ultraviolet laser beam;
a polygon scanner having a plurality of reflective facets, wherein the polygon scanner deflects the ultraviolet laser beam along a fast axis;
a telephoto lens assembly that receives the deflected ultraviolet laser beam from the polygon scanner, wherein the telephoto lens assembly comprising a positive lens group and a negative lens group that expand the deflected ultraviolet laser beam;
an objective lens configured to focus the expanded ultraviolet laser beam onto a tissue sample;
a motorized stage having at least two axes of motion, including at least one axis of an imaging plane and an axis orthogonal to the imaging plane, wherein the motorized stage is configured to support the tissue sample and configured to translate the tissue sample along the at least one axis of the imaging plane and vertically along the orthogonal axis;
an ultrasound transducer that is configured to detect photoacoustic signals generated from the tissue sample in response to illumination by the ultraviolet laser beam;
a data acquisition device that digitizes the photoacoustic signals; and
a controller that:
controls the motorized stage and is configured to perform a rapid pre-scan of the tissue sample;
extracts surface topology data from the photoacoustic signals acquired during the pre-scan to generate a contour map representing variations in surface height of the tissue sample;
synchronizes operation of the pulsed laser source, the polygon scanner, the motorized stage, and the data acquisition device during imaging; and
controls the motorized stage and is configured to dynamically adjust a position of the tissue sample vertically along the orthogonal axis during a high-resolution imaging scan based on the contour map.

2. The system of claim 1, comprising a nonlinear crystal positioned in an optical path of a laser beam at a first wavelength emitted by the pulsed laser source, wherein the nonlinear crystal converts the laser beam of the first wavelength to generate the ultraviolet laser beam through harmonic generation.

3. The system of claim 1, comprising:
an optical fiber having a stripped tip positioned at a beginning of a scanning trajectory of the ultraviolet laser beam; and a photodiode optically coupled to the optical fiber, wherein the photodiode generates a start-of-scan timing signal when the deflected ultraviolet laser beam strikes the stripped tip of the optical fiber.

4. The system of claim 1, wherein:

the ultrasound transducer is to detect the photoacoustic signals in a transmission mode of signal detection;

in a first configuration, the ultrasound transducer comprises a cylindrically focused transducer providing a one-dimensional (1D) line focus for signal detection, wherein the ultraviolet laser beam is confocal with the 1D line focus and is scanned along the 1D line focus; and in a second configuration, the ultrasound transducer is arranged in a linear ultrasound transducer array such that transducer elements detect signals from an illuminated spot on the tissue sample.

5. The system of claim 1, wherein the ultrasound transducer is to detect photoacoustic signals in a reflection mode of signal detection, and wherein the ultrasound transducer comprises a cylindrically focused transducer element having a central rectangular slit aperture that permits coaxial transmission of the ultraviolet laser beam therethrough.

6. The system of claim 1, comprising:

a right-angle prism and a rhomboid prism separated by an optical coupling medium, wherein the ultrasound transducer is to detect photoacoustic signals in a reflection mode of signal detection, wherein the rhomboid prism includes an acoustic cylindrical lens ground into a surface thereof, wherein the right-angle prism includes an optical correction lens ground on a top surface thereof, wherein the ultrasound transducer is mounted on the rhomboid prism and acoustically coupled thereto, and wherein the right-angle prism and the rhomboid prism guide the ultraviolet laser beam and acoustic waves to a common focal region.

7. The system of claim 1, comprising a processor that executes a conditional diffusion model comprising a neural network, wherein the processor transforms photoacoustic microscopy images into virtual histologically-stained images.

8. The system of claim 7, wherein the processor executes a semantic segmentation network to identify tumor regions and non-tumor regions in the virtual histologically-stained images.

9. The system of claim 1, comprising a processor that:

analyzes photoacoustic microscopy images acquired from the tissue sample using ultraviolet laser excitation;

applies a conditional diffusion model to the photoacoustic microscopy images to generate virtual histologically-stained images, wherein the conditional diffusion model comprises a denoising neural network trained to reverse a forward diffusion process while being conditioned on the photoacoustic microscopy images; and outputs the virtual histologically-stained images for pathology assessment.

10. The system of claim 9, wherein the processor preprocess the photoacoustic microscopy images prior to applying the conditional diffusion model by performing at least one of background flattening, global intensity normalization, filter-based denoising, or multi-channel enhancement.

11. The system of claim 9, wherein the conditional diffusion model generates the virtual histologically-stained images at a higher resolution than the photoacoustic microscopy images through learned upsampling.

12. The system of claim 9, wherein the processor applies a semantic segmentation network to the virtual histologically-stained images to generate a segmentation map identifying tumor regions and non-tumor regions.

13. The system of claim 12, wherein the semantic segmentation network receives as input both the virtual histologically-stained images and the photoacoustic microscopy images.

14. The system of claim 12, wherein the semantic segmentation network is trained using a loss function comprising at least one of Dice loss, cross-entropy loss, or boundary-aware regularization terms.

15. A method for rapid intraoperative pathology imaging, the method comprising:

generating an ultraviolet laser beam;

deflecting the ultraviolet laser beam using a rotating polygon scanner along a fast axis;

directing the deflected ultraviolet laser beam through a telephoto lens assembly comprising a positive lens group and a negative lens group to expand the deflected ultraviolet laser beam;

focusing the expanded ultraviolet laser beam onto a surface of a tissue sample using an objective lens;

performing a pre-scan of the tissue sample by:

raster scanning the ultraviolet laser beam across the tissue sample with a reduced resolution relative to a subsequent high-resolution imaging scan, detecting photoacoustic signals generated during the pre-scan, and extracting surface topology information from time-of-flight data contained in the photoacoustic signals to generate a contour map;

performing a high-resolution imaging scan by:

raster scanning the ultraviolet laser beam across the tissue sample, dynamically adjusting a position of the tissue sample along an orthogonal axis in real-time based on the contour map to maintain the surface within an optical depth of focus, and detecting photoacoustic signals to generate pathology images.

16. The method of claim 15, wherein generating the ultraviolet laser beam comprises:

emitting a pulsed laser beam at a first wavelength; and converting the first wavelength to an ultraviolet wavelength through second harmonic generation using a nonlinear crystal.

17. The method of claim 15, comprising:

detecting a start-of-scan signal using an optical fiber positioned at a beginning of a scanning trajectory; and synchronizing laser pulsing, data acquisition, and stage movement based on the start-of-scan signal.

18. The method of claim 15, wherein detecting photoacoustic signals comprises detecting the photoacoustic signals in transmission mode using a cylindrically focused ultrasound transducer positioned opposite to an illumination side of the tissue sample.

19. The method of claim 15, wherein detecting photoacoustic signals comprises detecting the photoacoustic signals in reflection mode through a cylindrically focused ultrasound transducer with a slit aperture, wherein the ultraviolet laser beam passes coaxially through the slit aperture.

20. The method of claim 15, comprising applying a conditional diffusion model to the pathology images to generate virtual histologically-stained images that simulate conventional histological staining without physical staining of the tissue sample.

21. The method of claim 20, comprising applying a semantic segmentation network to the virtual histologically-stained images to automatically detect tumor margins within the tissue sample.

22. The method of claim 15, comprising:

training a conditional diffusion model for virtual staining
    using training data comprising:
        photoacoustic microscopy images acquired with ultra-
           violet laser excitation; and
        corresponding histologically-stained images,
    wherein the conditional diffusion model is trained using
        a loss function comprising at least one of reconstruc-
        tion loss, perceptual loss, adversarial loss, structural
        preservation loss, or segmentation consistency loss;
        and
training a semantic segmentation network for tumor mar-
    gin detection using annotated datasets comprising
    labeled tumor regions and non-tumor regions.

* * * * *